US010227589B2

(12) United States Patent
Mukherjee et al.

(10) Patent No.: US 10,227,589 B2
(45) Date of Patent: Mar. 12, 2019

(54) METHOD FOR INHIBITING TUMOR GROWTH THROUGH RNA-INTERFERENCE USING LIPOSOMALLY ASSOCIATED CDC20 SIRNA

(71) Applicant: COUNCIL OF SCIENTIFIC AND INDUSTRIAL RESEARCH, New Delhi (IN)

(72) Inventors: Anubhab Mukherjee, Andhra Pradesh (IN); Jayanta Bhattacharyya, Andhra Pradesh (IN); Arabinda Chaudhuri, Andhra Pradesh (IN)

(73) Assignee: COUNCIL OF SCIENTIFIC AND INDUSTRIAL RESEARCH, New Delhi (IN)

( * ) Notice: Subject to any disclaimer, the term of this patent is extended or adjusted under 35 U.S.C. 154(b) by 0 days.

(21) Appl. No.: 14/761,083

(22) PCT Filed: Jan. 28, 2013

(86) PCT No.: PCT/IN2013/000054
§ 371 (c)(1),
(2) Date: Jul. 15, 2015

(87) PCT Pub. No.: WO2014/115158
PCT Pub. Date: Jul. 31, 2014

(65) Prior Publication Data
US 2016/0010088 A1    Jan. 14, 2016

(51) Int. Cl.
*C12N 15/113*    (2010.01)
*C12N 15/11*    (2006.01)

(52) U.S. Cl.
CPC .......... *C12N 15/113* (2013.01); *C12N 15/111* (2013.01); *C12N 15/1135* (2013.01); *C12N 2310/14* (2013.01); *C12N 2310/531* (2013.01); *C12N 2320/32* (2013.01)

(58) Field of Classification Search
CPC .............. C12N 15/113; C12N 2310/14; A01K 2207/05
See application file for complete search history.

(56) References Cited

U.S. PATENT DOCUMENTS

| | | | | |
|---|---|---|---|---|
| 2005/0064595 | A1* | 3/2005 | MacLachlan | A61K 9/1272 435/458 |
| 2007/0185320 | A1* | 8/2007 | Khvorova | C12N 15/111 536/23.1 |
| 2009/0137045 | A1* | 5/2009 | Balaban | C12N 15/87 435/455 |
| 2012/0046186 | A1* | 2/2012 | Pelham | C12Q 1/6886 506/9 |
| 2012/0121689 | A1* | 5/2012 | Bacon | A61K 9/127 424/450 |
| 2012/0308642 | A1* | 12/2012 | Dash | A61K 31/713 424/450 |

FOREIGN PATENT DOCUMENTS

WO    WO2006074546 A1 *    7/2006
WO    2010/113172 A1    10/2010

OTHER PUBLICATIONS

Semple et al. Nature Biotechnology 2010, 28:172-178.*
Pramanik et al.: "Lipopeptide with a RGDK Tetrapeptide Sequence Can Selectively Target Genes to Proangiogenic #5#1Integrin Receptor and Mouse Tumor Vasculature", Journal of Medicinal Chemistry, vol. 51, Issue 22, Nov. 27, 2008, pp. 7298-7302.
Rajesh et al.: "Dramatic Influence of the Orientation of Linker between Hydrophilic and Hydrophobic Lipid Moiety in Liposomal Gene Delivery", Journal of the American Chemical Society, vol. 129, Issue 37, Sep. 19, 2007, pp. 11408-11420.
Rao, N. Madhusudhana: "Cationic Lipid-Mediated Nucleic Acid Delivery: Beyond Being Cationic", Chemistry and Physics of Lipids, vol. 163, Issue 3, Mar. 2010, pp. 245-252.
Reich et al.: "Small interfering RNA (siRNA) targeting VEGF effectively inhibits ocular neovascularization in a mouse model", Molecular Vision, vol. 9, May 30, 2003, pp. 210-216.
Sen et al.: "Design, Syntheses, and Transfection Biology of Novel Non-Cholesterol-Based Guanidinylated Cationic Lipids", Journal of Medicinal Chemistry, vol. 48, Issue 3, Feb. 10, 2005, pp. 812-820.
Shankar et al.: "The Prospect of Silencing Disease Using RNA Interference", The Journal of the American Medical Association, vol. 293, No. 11, Mar. 16, 2005, pp. 1367-1373.
Shen et al.: "Suppression of ocular neovascularization with siRNA targeting VEGF receptor 1", Gene Therapy, vol. 13, Feb. 2006, pp. 225-234.
Singh et al.: "Anchor Dependency for Non-Glycerol Based Cationic Lipofectins: Mixed Bag of Regular and Anomalous Transfection Profiles", Chemistry—A European Journal, vol. 8, No. 4, Feb. 15, 2002, pp. 900-909.
Singh et al.: "On the Gene Delivery Efficacies of pH-Sensitive Cationic Lipids via Endosomal Protonation: A Chemical Biology Investigation", Chemistry & Biology, vol. 11, May 2004, pp. 713-723.
Singh et al.: "Single additional methylene group in the head-group region imparts high gene transfer e/cacy to a transfection-incompetent cationic lipid", FEBS Letters, vol. 556, Jan. 2, 2004, pp. 86-90.

(Continued)

*Primary Examiner* — Brian Whiteman
(74) *Attorney, Agent, or Firm* — Merchant & Gould P.C.

(57) ABSTRACT

Liposomal compositions comprising of liposomes of guanidinylated cationic amphiphiles as the main lipid and cholesterol/1,2-dioleoyl-sn-glycero-3-phosphocholine (DOPC)/aminopropyl polyethyleneglycol carbamyl-distearoylphosphatidyl-ethanolamine (DSPE-peg-NH$_2$) as co-lipids are described. These liposomal compositions containing encapsulated or electrostatically complexed therapeutic small interfering RNAs (siRNAs) against Cdc20, a key cell cycle regulator, inhibit solid tumor growth and melanoma tumor growth on lung in C57BL/6J mice.

14 Claims, 12 Drawing Sheets
Specification includes a Sequence Listing.

(56) References Cited

OTHER PUBLICATIONS

Song et al.: "RNA interference targeting Fas protects mice from fulminant hepatitis", Nature Medicine, vol. 9, No. 3, Mar. 2003, pp. 347-351.
Takei et al.: "A Small Interfering RNA Targeting Vascular Endothelial Growth Factor as Cancer Therapeutics", Cancer Research, vol. 64, Issue 10, May 15, 2004, pp. 3365-3370.
Taniguchi et al.: "Targeting of CDC20 via Small Interfering RNA Causes Enhancement of the Cytotoxicity of Chemoradiation", Anticancer Research, vol. 28, Issue 3A, May-Jun. 2008, pp. 1559-1563.
Tompkins et al.: "Protection against lethal influenza virus challenge by RNA interference in vivo", Proceedings of the National Academy of Sciences of the United States of America, vol. 101, No. 23, Jun. 8, 2004, pp. 8682-8686.
Vandenburg et al.: "Non-Leaky Vesicle Fusion and Enhanced Cell Transfection Using a Cationic Facial Amphiphile", Journal of the American Chemical Society, vol. 122, Issue 13, Apr. 5, 2000, pp. 3252-3253.
Verma et al.: "Small Interfering RNAs Directed against β-Catenin Inhibit the in Vitro and in Vivo Growth of Colon Cancer Cells", Clinical Cancer Research, vol. 9, Issue 4, Apr. 2003, pp. 1291-1300.
Vigneron et al.: "Guanidinium-cholesterol cationic lipids: Efficient vectors for the transfection of eukaryotic cells", Proceedings of the National Academy of Sciences of the United States of America, vol. 93, Sep. 1996, pp. 9682-9686.
Wang et al.: "Synthesis and Characterization of Long Chain Alkyl Acyl Carnitine Esters. Potentially Biodegradable Cationic Lipids for Use in Gene Delivery", Journal of Medicinal Chemistry, vol. 41, Issue 13, pp. 2207-2215.
Wheeler et al.: "A novel cationic lipid greatly enhances plasmid DNA delivery and expression in mouse lung", Proceedings of the National Academy of Sciences of the United States of America, vol. 93, Oct. 1996, pp. 11454-11459.
Written Opinion of the International Searching Authority for International Patent Application No. PCT/IN2013/000054 (dated Oct. 29, 2013).
Xie et al.: "Harnessing in vivo siRNA delivery for drug discovery and therapeutic development", Drug Discovery Today, vol. 11, No. 1/2, Jan. 2006, pp. 67-73.
Zender et al.: "Caspase 8 small interfering RNA prevents acute liver failure in mice", Proceedings of the National Academy of Sciences of the United States of America, vol. 100, No. 13, Jun. 24, 2003, pp. 7797-7802.
International Preliminary Report on Patentability for corresponding International Patent Application No. PCT/IN2013/000054 (dated Jul. 28, 2015).
Aristarkhov et al.: "E2-C, a cyclin-selective ubiquitin carrier protein required for the destruction of mitotic cyclins", Proceedings of the National Academy of Sciences of the United States of America, vol. 93, Apr. 1996, pp. 4294-4299.
Banerjee et al.: "Design, Synthesis, and Transfection Biology of Novel Cationic Glycolipids for Use in Liposomal Gene Delivery", Journal of Medicinal Chemistry, vol. 44, Issue 24, Nov. 22, 2001, pp. 4176-4185.
Banerjee et al.: "Novel Series of Non-Glycerol-Based Cationic Transfection Lipids for Use in Liposomal Gene Delivery", Journal of Medicinal Chemistry, vol. 42, Issue 21, Oct. 21, 1999, pp. 4292-4299.
Behr et al.: "Efficient gene transfer into mammalian primary endocrine cells with lipopolyamine-coated DNA", Proceedings of the National Academy of Sciences of the United States of America, vol. 86, Sep. 1989, pp. 6982-6986.
Bennett et al.: "Cationic Lipid-Mediated Gene Delivery to Murine Lung: Correlation of Lipid Hydration with in Vivo Transfection Activity", Journal of Medicinal Chemistry, vol. 40, Issue 25, Dec. 5, 1997, pp. 4069-4078.
Bitko et al.: "Inhibition of respiratory viruses by nasally administered siRNA", Nature Medicine, vol. 11, No. 1, Jan. 2005, pp. 50-55.

Blessing et al.: "Template Oligomerization of DNA-Bound Cations Produces Calibrated Nanometric Particles", Journal of the American Chemical Society, vol. 120, Issue 33, Aug. 26, 1998, pp. 8519-8520.
Bridge et al.: "Induction of an interferon response by RNAi vectors in mammalian cells", Nature Genetics, vol. 34, No. 3, Jul. 2003, pp. 263-264.
Davis et al.: "Evidence of RNAi in humans from systemically administered siRNA via targeted nanoparticles", Nature, vol. 464, Apr. 15, 2010, pp. 1067-1070.
Dolan et al: "Cell uptake and cytotoxicity of a novel cyclometalated iridium(III) complex and its octaarginine peptide conjugate", Journal of Inorganic Biochemistry, vol. 119, Feb. 2013, pp. 65-74.
Elbashir et al.: "Duplexes of 21-nucleotide RNAs mediate RNA interference in cultured mammalian cells", Nature, vol. 411, May 24, 2001, pp. 494-498.
Felgner et al.: "Lipofection: A Highly Efficient, Lipid-Mediated DNA-Transfection Precedure", Proceedings of the National Academy of Sciences of the United States of America, vol. 84, Nov. 1987, pp. 7413-7417.
Ferrari et al.: "Trends in lipoplex physical properties dependent on cationic lipid structure, vehicle and complexation procedure do not correlate with biological activity", Nucleic Acids Research, vol. 29, No. 7, 2001, pp. 1539-1548.
Filleur et al.: "SiRNA-mediated Inhibition of Vascular Endothelial Growth Factor Severely Limits Tumor Resistance to Antiangiogenic Thrombospondin-1 and Slows Tumor Vascularization and Growth", Cancer Research, vol. 63, Issue 14, Jul. 15, 2003, pp. 3919-3922.
Fire et al.: ""Potent and specific genetic interference by double-stranded RNA in Caenorhabditis elegans", Nature, vol. 391, Feb. 19, 1998, pp. 806-811.".
Ge et al.: "Inhibition of influenza virus production in virus-infected mice by RNA interference", Proceedings of the National Academy of Sciences of the United States of America, vol. 101, No. 23, Jun. 8, 2004, pp. 8676-8681.
Giladi et al.: "Small Interfering RNA Inhibits Hepatitis B Virus Replication in Mice", Molecular Therapy, vol. 8, No. 5, Nov. 2003, pp. 769-776.
Glotzer et al.: "Cyclin is degraded by the ubiquitin pathway", Nature, vol. 349, Jan. 10, 1991, pp. 132-138.
Hamada et al.: "Increased Expression of the Genes for Mitotic Spindle Assembly and Chromosome Segregation in Both Lung and Pancreatic Carcinomas", Cancer Genomics & Proteomics, vol. 1, Issue 3, May-Jun. 2004, pp. 231-240.
Hamar et al.: "Small interfering RNA targeting Fas protects mice against renal ischemia-reperfusion injury", Proceedings of the National Academy of Sciences of the United States of America, vol. 101, No. 41, Oct. 12, 2004, pp. 14883-14888.
He et al.: "MicroRNAs: Small RNAs With a Big Role in Gene Regulation", Nature Reviews: Genetics, vol. 5, Jul. 2004, pp. 522-531.
Hutvágner et al: "A microRNA in a Multiple-Turnover RNAi Enzyme Complex", Science, vol. 297, Sep. 20, 2002, pp. 2056-2060.
International Search Report for corresponding International Patent Application No. PCT/IN2013/000054 (dated Oct. 29, 2013).
Jeffs et al.: "A Scalable, Extrusion-Free Method for Efficient Liposomal Encapsulation of Plasmid DNA", Pharmaceutical Research, vol. 22, No. 3, Mar. 2005, pp. 362-372.
Karmali et al.: "Cationic Liposomes as Non-Viral Carriers of GeneMedicines: Resolved Issues, Open Questions, and Future Promises", Medicinal Research Reviews, vol. 27, No. 5, Sep. 2007, pp. 696-722.
Karmali et al.: "Design, Syntheses and in Vitro Gene Delivery Efficacies of Novel Mono-, Di- and Trilysinated Cationic Lipids: A Structure-Activity Investigation", Journal of Medicinal Chemistry, vol. 47, Issue 8, Apr. 8, 2004, pp. 2123-2132.
Kidokoro et al.: "CDC20, a potential cancer therapeutic target, is negatively regulated by p53", Oncogene, vol. 27, Issue 11, Mar. 6, 2008, pp. 1562-1571.
Kim er al.: "Identification of Gastric Cancer-Related Genes Using a cDNA Microarray Containing Novel Expressed Sequence Tags Expressed in Gastric Cancer Cells", Clinical Cancer Research, vol. 11, Issue 3, Feb. 8, 2005, pp. 473-482.

(56) References Cited

OTHER PUBLICATIONS

Kim et al.: "Strategies for silencing human disease using RNA interference", Nature Reviews: Genetics, vol. 8, Mar. 2007, pp. 173-184.
Kim et al.: "Synthetic dsRNA Dicer substrates enhance RNAi potency and efficacy", Nature Biotechnology, vol. 23, No. 2, Feb. 2005, pp. 222-226.
King et al.: "A 20S Complex Containing CDC27 and CDC16 Catalyzes the Mitosis-Specific Conjugation of Ubiquitin to Cyclin B", Cell, vol. 81, Apr. 21, 1995, pp. 279-288.
Kumar et al.: "On the disulfide-linker strategy for designing efficacious cationic transfection lipids: an unexpected transfection profile", FEBS Letters, vol. 571, Jul. 30, 2004, pp. 205-211.
Kumar et al.: "Single histidine residue in head-group region issufficient to impart remarkable gene transfection properties to cationic lipids: evidence for histidinemediated membrane fusion at acidic pH", Gene Therapy, vol. 10, 2003, pp. 1206-1215.
Leng et al.: "Small interfering RNA targeting Raf-1 inhibits tumor growth in vitro and in vivo", Cancer Gene Therapy, vol. 12, Apr. 1, 2005, pp. 682-690.
Li et al.: "Efficient Oncogene Silencing and Metastastasis Inhibition via Systemic Delivery of siRNA", Molecular Therapy, vol. 16, No. 5, May 2008, pp. 942-946.
Liang et al.: "Silencing of CXCR4 Blocks Breast Cancer Metastasis", Cancer Research, vol. 65, Issue 3, Feb. 1, 2005, pp. 967-971.
Lim et al.: "A Self-Destroying Polycationic Polymer: BiodegradablePoly(4-hydroxy-L-proline ester)", Journal of the American Chemical Society, vol. 121, Issue 33, Jun. 23, 1999, pp. 5633-5639.
Lim et al.: "Development of a Safe Gene Delivery System UsingBiodegradable Polymer, Poly[r-(4-aminobutyl)-L-glycolic acid]", Journal of the American Chemical Society, vol. 122, Issue 27 Jul. 12, 2000, pp. 6524-6525.
Lynn et al.: "Degradable Poly(β-amino esters): Synthesis, Characterization, and Self-Assembly with Plasmid DNA", Journal of the American Chemical Society, vol. 122, Issue 44, Nov. 8, 2000, pp. 10761-10768.
Mahidhar et al.: "Distance of Hydroxyl Functionality from the Quaternized Center Influence DNA Binding and in Vitro Gene Delivery Efficacies of Cationic Lipids with Hydroxyalkyl Headgroups", Journal of Medicinal Chemistry, vol. 47, Issue 23, Nov. 4, 2004, pp. 5721-5728.
Mahidhar et al.: "Spacer-Arm Modulated Gene Delivery Efficacy of Novel Cationic Glycolipids: Design, Synthesis, and in Vitro Transfection Biology", Journal of Medicinal Chemistry, vol. 47, Issue 16, Jul. 29, 2004, pp. 3938-3948.
Majeti et al.: "Example of Fatty Acid-Loaded Lipoplex in Enhancing in Vitro Gene Transfer Efficacies of Cationic Amphiphile", Bioconjugate Chemistry, vol. 16, Issue 3, May 2005, pp. 676-684.
Majeti et al.: "In Vitro Gene Transfer Efficacies of N,N-Dialkylpyrrolidinium Chlorides: A Structure-Activity Investigation", Journal of Medicinal Chemistry, vol. 48, Issue 11, Jun. 2, 2005, pp. 3784-3795.
Matranga et al.: "Passenger-Strand Cleavage Facilitates Assembly of siRNA into Ago2-Containing RNAi Enzyme Complexes", Cell, vol. 123, Nov. 18, 2005, pp. 607-620.
Meister et al.: "Mechanisms of gene silencing by double-stranded RNA", Nature, vol. 431, Sep. 16, 2004, pp. 343-349.
Mukherjee et al.: "Common co-lipids, in synergy, impart high gene transfer properties to transfection-incompetent cationic lipids", FEBS Letters, vol. 579, Issue 5, Feb. 14, 2005, pp. 1291-1300.
Mukherjee et al.: "Liposomally Encapsulated CDC20 siRNA inhibits both solid melanoma tumor growth and spontaneous growth of intravenously injected melanoma cells on mouse lung", Drug Delivery and Translational Research, Jun. 2013, vol. 3, Issue 3, pp. 224-234.
Mukherjee et al.: "Supplementary Material: Liposomally Encapsulated CDC20 siRNA inhibits both solid melanoma tumor growth and spontaneous growth of intravenously injected melanoma cells on mouse lung", Drug Delivery and Translational Research, vol. 3, No. 3, Mar. 23, 2013 (Mar. 23, 2013), pp. 1-4, XP002715033.
Nogawa et al.: "Intravesical administration of small interferingRNA targeting PLK-1 successfully prevents the growth of bladder cancer", The Journal of Clinical Investigation, vol. 115, No. 4, Apr. 1, 2005, pp. 978-985.
Peer et al.: "Selective gene silencing in activated leukocytes by targeting siRNAs to the integrin lymphocyte function-associated antigen-1", Proceedings of the National Academy of Sciences of the United States of America, vol. 104, No. 10, Mar. 6, 2007, pp. 4095-4100.

\* cited by examiner

Lipid 1: $R_1 = R_2 = $ n-$C_{14}H_{29}$
Lipid 2: $R_1 = R_2 = $ n-$C_{16}H_{33}$
Lipid 3: $R_1 = R_2 = $ n-$C_{18}H_{37}$ Sequences of the synthetic human CDC20 siRNA Sense      :   5' r(CCACCAUGAUGUUCGGGUA) d(TT) 3'

Antisense  :   5' r(UACCCGAACAUCAUGGUGG) d(TG)3'

Sequences of the synthetic mouse CDC20 siRNA

Sense      :   5' r(AGUUCGUAUCAACCUUAAA) d(TT) 3'
Antisense  :   5' r(UUUAAGGAAGAUACGAACU) d(TG)3'

METHOD FOR INHIBITING TUMOR GROWTH THROUGH RNA-INTERFERENCE USING LIPOSOMALLY ASSOCIATED CDC20 SIRNA

This application is a National Stage Application of PCT/IN2013/000052, filed Jan. 28, 2013, and which application is incorporated herein by reference. To the extent appropriate, a claim of priority is made to each of the above disclosed applications.

FIELD OF INVENTION

The present invention provides an in-vivo method for treating cancer in a warm-blooded animal, comprising administering a therapeutically effective amount of the liposomal composition characterized in having small interfering RNAs (siRNAs) against Cdc20 (a key cell cycle regulator) useful for inhibiting tumour growth. The present invention also provides pharmaceutical compositions for efficient in vitro and in vivo delivery of RNA molecules such as small interfering RNAs (siRNAs), plasmid encoded short hairpin RNAs (shRNAs), etc. The present invention also provides methods and compositions for silencing expression of therapeutic genes under both in vitro and in vivo settings by down regulation of mRNAs. Furthermore, the present invention demonstrates the systemic potential of siRNA and shRNA against Cdc20 (a key cell cycle regulator) in inhibiting growth of solid tumor and growth of melanoma in lung in C57BL/6J mice. The area of medical science that is likely to benefit most from the present invention is therapy of inherited diseases through RNA interference.

BACKGROUND AND PRIOR ART INFORMATION

RNAi therapeutics are emerging new ways to combat human diseases through silencing of undesired gene expressions. The discovery of long double-stranded RNA mediated RNAi in the worm (Fire, A. et al. Nature 1998; 391:806-811) followed by demonstration of RNAi mediated by small interfering RNA (siRNA) in mammalian cells (Elbashir, S. M. et al. Nature 2001; 411:494-498) have generated an unprecedented global interest in RNAi therapeutics. The small RNA molecules involved in RNAi pathways include small interfering RNAs (siRNAs) and microRNAs (miRNAs) with the latter deriving from imperfectly paired non-coding hairpin RNA structures those are naturally transcribed by the genome (Meister, G. and Tuschi, T. Nature 2004; 431:343-349; Kim, D. H. and *Rossi*, J. J. Nature Rev Genet 2007; 8:175-184). siRNA mediates gene silencing through sequence specific cleavage of perfectly complementary messenger RNA (mRNA) whereas gene silencing by miRNAs are mediated through translational repression and transcript degradation for imperfectly complementary target messenger RNAs. The steps involved in the endogenous production of microRNAs include: (a) processing of RNAs with stems or short-hairpin structures (encoded in the intragenic regions or within the introns) in the nucleus to form precursor RNA molecules called pre-microRNAs; (b) export of the pre-microRNAs from the nucleus into the cell cytoplasm; (C) further shortening and processing of the pre-miRNAs by an RNase III enzyme called Dicer to produce an imperfectly matched, double-stranded miRNA (Kim, D. H. and *Rossi*, J. J. Nature Rev Genet 2007; 8:175-184; He, L. and Hannon, G. J. Nature Rev Genet 2004; 5:522-531). Dicer similarly processes long, perfectly matched dsRNA into siRNAs. A multi-enzyme complex including the Argonoute 2 (AGO2) and the RNA-induced silencing complex (RISC) binds to either the microRNA duplex or the siRNA duplex and discards one strand forming an activated complex containing the guide or antisense strand (Mantranga, C. et al. Cell 2005; 123:607-620). The activated AGO2-RISC complex then induces silencing of gene expression by binding with the mRNA strand of complementary sequence followed by its subsequent cleavage. Gene silencing through mRNA cleavage owes its potency to the rapid nucleolytic degradation of the mRNA fragments. Once the mRNA is degraded, the activated RISC complex becomes free to bind and cleave another target mRNA in a catalytic fashion (Hutvagner, C and Zamore, P. D. Science 2002; 297:2056-2060). The first in vivo study on RNAi-based therapeutics was disclosed in an animal disease model in 2003 (Song, E. et al. Nat. Med. 2003; 9:347-351). Ever since then, a plethora of in vivo studies on RNAi therapeutics have been reported. siRNA mediated inhibitions of vascular endothelial growth factor have been demonstrated to be capable of suppressing tumor vascularization and growth in mice (Filleur, S. et al. Cancer Res. 2003; 63:3919-3922, Takei, Y. et al. Cancer Res. 2004; 64:3365-3370) as well as in inhibiting ocular neovascularization in a mouse model (Reich, S J et al. Mol. Vis. 2003; 9:210-216). Galun, E. demonstrated that replication of hepatitis B virus in mice can be inhibited by siRNA (Mol. Ther. 2003; 8:769-776). Small interfering RNA directed against beta-catenin has been shown to inhibit the in vitro and in vivo growth of colon cancer cells (Verma, U N et al. Clin. Cancer Res. 2003; 9:1291-1300). Caspase 8, small interfering RNA has been shown to be capable of preventing acute liver failure in mice (Zender, L. et al. Proc. Natl. Acad. Sci. USA. 2003; 100:7797-7802) Inhibition of influenza virus production in virus-infected mice has been achieved through RNA interference (Ge, Q. et al. Proc. Natl. Acad. Sci. USA. 2004; 101:8676-8681, Tompkins, S M et al. Proc. Natl. Acad. Sci. USA. 2004; 101:8682-8686). Use of siRNA targeting Fas has been used to protect mice against renal ischemia-reperfusion injury (Hamar, P. et al. Proc. Natl. Acad. Sci. USA. 2004; 101:14883-14888). Small interfering RNA, upon nasal administration, has been shown to inhibit respiratory viruses (Bitko, V. et al. Nat. Med. 2005; 11:50-55). siRNA targeting Raf-1 can inhibit tumor growth both in vitro and in vivo (Leng, Q. and Mixson, A J. Cancer Gen. Ther. 2005; 12:682-690). Small interfering RNA against CXCR-4 blocks breast cancer metastasis (Liang Z. et al. Cancer Res. 2005; 65:967-971). Intravesical administration of siRNA targeting PLK-1 successfully prevented the growth of bladder cancer (Nogawa, M. et al. J. Clin. Invest. 2005; 115:978-985). Suppression of ocular neovascularization with siRNA targeting VEGF receptor 1 has been achieved (Shen, J. et al. Gene Ther. 2006; 13:225-234). Selective gene silencing in activated leukocytes has been demonstrated by targeting siRNA to the integrin lymphocyte function-associated antigen (Peer, D. et al. Proc. Natl. Acad. Sci. USA. 2007; 104:4095-4100). Recently, RNAi in human has been demonstrated (Davis, M. E. et al. Nature 2010; 464:1067-70).

Cell division cycle 20 (Cdc20) is an essential cell cycle regulator required for the completion of mitosis in organisms from yeast to human. In the cell cycle, activation of the anaphase-promoting complex (APC) is required for anaphase initiation and for exit from mitosis. Cdc20 is one of the key regulators for APC; it binds to APC and activates its cyclin ubiquitination activity (Glotzer, M., Murray, A. W., and Kirschner, M. W. (1991) Nature, 349, 132-138). This complex recognizes a 9 amino acid sequence (destruction box [D-box]) in the N terminus of cyclin and a few other proteins, catalyzing the transfer of ubiquitin from the thioester of a UBC-ubiquitin complex to a free amino group on the protein and then linking further ubiquitins to the ubiquitinated substrate to generate a large chain of ubiquitins; the tagged protein is then recognized by the proteasome and degraded (King, R W. et al. (1995) Cell, 81, 279-288. Aristarchus, A. et al. (1996) Proc. Natl. Acad. Sci. USA, 93, 4294-9). In metaphase, sister chromatids cannot separate as they are held together at their centromeres and along the chromosome arms by multiprotein complex of SMC family, named cohesins. Again, the SMC cohesion proteins are associated by Sccl protein. Before anaphase, securin binds to and inhibits separase, a ubiquitous protease. At the onset of anaphase, when all the chromosome kinetochores have arranged in the spindle microtubules, APC/Cdc20 complexes polyubiquitinates securin. Thus, securin is degraded by proteases and the free separase now cleaves Sccl making the sister chromatid free. The pole ward force exerted on kinetochores pulls the sister chromatids towards the opposite spindle poles. Since Cdc20 is highly expressed in several carcinomas [Hamada, K. et al. (2004) Cancer Gen Prot 1: 231-240, Kim, J M. et al. (2005). Clin Cancer Res 11: 473-482.], knockdown of the expression of Cdc20 through RNA interference holds therapeutic promise in combating cancer. Recently, at the cellular level, it has been reported that Cdc20 siRNA can inhibit more than 90% Cdc20 expression at both the transcriptional and translational levels and the specific knockdown of Cdc20 expression inhibited the cell growth of human pancreatic carcinoma cells in vitro [Taniguchi, K. et al. (2008). Anticancer Res 28: 1559-1563].

Guanidinylated cationic amphiphiles are, in general, efficient in delivering genetic materials into cells. Many distinguishing factors contribute to the high gene transfer efficiencies of guanidinylated cationic amphiphiles. The guanidinium head-groups remain protonated over a much wider range than other basic groups due to its remarkably high pka values (13.5) and therefore they strongly bind with polyanionic macromolecular DNA molecules under the physiological pH; in addition to forming electrostatic complexes with genetic materials, they form characteristic parallel zwitterionic N—H+ . . . O—hydrogen bonds with the phosphate ions of the nucleotides and they are capable of forming hydrogen bonds with nucleic acid bases [Vigneron, J P. et al. (1996). Proc. Natl. Acad. Sci., USA 93: 9682-9686.]. Previously we have demonstrated that the guanidinylated cationic amphiphile with myristyl (n-C14H29) tail (lipid 1, FIG. 1a) is most efficient in delivering reporter gene into cultured animal cells at lipid:DNA charge ratio of 3:1 and 1:1 [Sen, J, Chaudhuri, A. (2005). J Med Chem 48: 812-820.].

Beyond identifying an active target sequence, a key challenge in the field of RNAi therapeutics is ensuring efficient delivery of small interfering RNAs inside the cell cytoplasm. Efficient intracellular delivery of biologically active compounds have previously been accomplished using liposomes, microscopic fatty bubbles of amphiphilic molecules which contain both hydrophobic (water hating) and hydrophilic (water loving) regions in their molecular architectures. Several methods for complexing biologically active compounds with liposomes have been developed. For instance, DOTMA (N-1-(2,3-dioleyloxy)propyl]-N,N,N-trimethylammonium chloride) was the first cationic amphiphile used to deliver biologically active polynucleotides (Felgner et al. Proc. Natl. Acad. Sci. USA. 1987; 84:7413-7417). Ever since then, a plethora of cationic amphiphiles have been used in delivering polynucleotides into the cell cytoplasm (Karmali, P. P. and Chaudhuri, A. Med. Res. Rev. 2007; 27:696-722 and the references cited therein). Cationic liposomes in particular, are least immunogenic. Manufacturing a greater degree of control can be exercised over the lipid's structure on a molecular level and the products can be highly purified. Use of cationic liposomes does not require any special expertise in handling and preparation techniques. Cationic liposomes can be covalently grafted with receptor specific ligands for accomplishing targeted gene delivery. Such multitude of distinguished favorable clinical features are increasingly making cationic liposomes as the non-viral transfection vectors of choice for delivering polynucleotide into body cells.

SUMMARY OF THE INVENTION

Accordingly, the present invention provides an in-vivo method for treating cancer in a warm-blooded animal, comprising administering a therapeutically effective amount of the liposomal composition characterized in having small interfering RNAs (siRNAs) against Cdc20 (a key cell cycle regulator) useful for inhibiting tumour growth. The present invention provides pharmaceutical compositions for delivering small RNA molecules inside the cytoplasm of cultured mammalian cells with high efficiency and low toxicity. In addition, the present invention provides compositions for knocking down the expression of a specific target gene by treating cells with the formulations comprising cationic lipid, a neutral colipid and a small RNA molecule. We demonstrate that our method delivers siRNA efficaciously into animal cells for the purpose of RNA interference. We also demonstrate that our method delivers shRNA efficaciously into animal cells for the purpose of RNA interference. The present invention provides compositions for silencing expression of therapeutic genes in vitro by down regulation of mRNA and thus by down regulation of respective protein. The present invention demonstrates the systemic potential of liposomally encapsulated siRNA against Cdc20 (a key cell cycle regulator) in inhibiting growth of melanoma in lung using a lung metastasis model in C57BL/6J mice. The present invention also demonstrates the systemic potential of liposomally bound shRNA against Cdc20 (a key cell cycle regulator) in inhibiting growth of solid tumor using a syngenic model in C57BL/6J mice. At the cellular level, the present invention provides the liposomal composition for delivery of mouse Cdc20 siRNA that silences the expression of Cdc20 in B16F10 cells at mRNA levels. At the cellular level, the present invention provides the liposomal composition for delivery of mouse Cdc20 siRNA that silences the expression of Cdc20 in B16F10 cells at protein levels. Again, at the cellular level, the present invention provides the liposomal composition for delivery of human Cdc20 siRNA that silences the expression of Cdc20 in A549 cells at mRNA levels. At the cellular level, the present invention provides the liposomal composition for delivery of human Cdc20 siRNA that silences the expression of Cdc20 in A549 cells at protein levels. At the cellular level, the Flow Cytometric analysis for the Cyclin B1 content (marker for G2/M phase of cell cycle) confirmed the presence of significantly enhanced populations of G2/M phase for B16F10 cells treated with liposomally bound mouse siRNA against Cdc20. At the cellular level, the Flow Cytometric analysis for the Cyclin B1 content (marker for G2/M phase of cell cycle) confirmed the presence of significantly enhanced populations of G2/M phase for A549 cells treated with liposomally bound human siRNA against Cdc20.

DETAILED DESCRIPTION OF THE INVENTION

Figure 1:
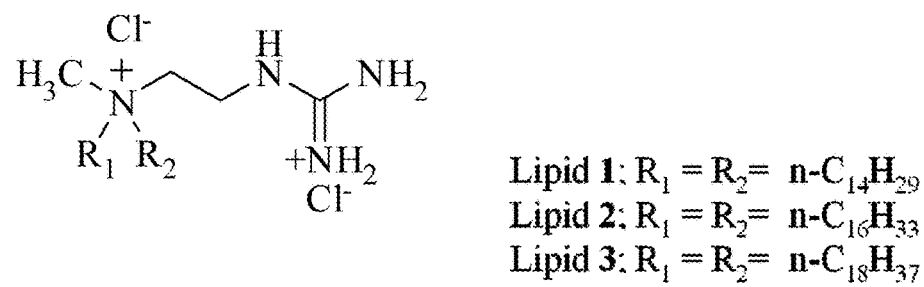
FIG. 1 shows the structures of the cationic transfection lipids used and sequences of the human and mouse siRNA against Cdc20. Structures of the guanidinylated cationic amphiphiles 1-3 (a) used for delivering Cdc20 siRNA and the sequences of the synthetic human Cdc20 siRNA (Seq ID No. 1 and 2) (b) and the mouse Cdc20 siRNA (Seq ID No. 3 and 4) (c) used.

The present invention provides pharmaceutical compositions for delivering small RNA molecules inside the cytoplasm of cultured mammalian cells with high efficiency and low toxicity.

Liposomes, in general, have long been viewed as biocompatible drug/gene delivery reagents owing to their structural similarity to cell membranes. They are spherical bilayers composed of individual lipids enclosing a watery interior. Each lipid possesses a hydrophilic head group attached via a linker to a large hydrophobic domain. When exposed to an aqueous environment, these amphiphiles spontaneously form large spherical structures known as liposomes above a certain critical vesicular concentration (CVC). Within the sphere, lipids are arranged back-to-back in bilayers with the polar hydrophilic group facing outwards shielding the hydrophobic domain from the aqueous solution. Liposomes may be unilamellar (composed of a single bilayer) or multilamellar (composed of many concentric bilayers). The multilamellar liposome (MLV) upon sonication followed by repeated extrusion through polycarbonate membranes of defined pore size assume the size of small unilamellar vesicle (SUV, 30-100 nm) or large unilamellar vesicle (LUV, 150-250 nm).

RNAi relies on an intracellular multistep process which can roughly be divided into the initiation phase and the subsequent effector phase. In the so-called initiation phase, RNaseIII Dicer cuts the dsRNAs of exogenous or endogenous origin into siRNAs. Apart from the size of 21-23 nucleotides, siRNAs have a few characteristic features that are essential for their function. They have been shown to contain 2-nucleotide 3' overhangs and 5'-phosporylated termini, which are typical features of RNaseIII cleavage products. miRNAs are formed by RNaseIII enzyme Drosha which cleaves pri-miRNA, originates by RNA polymerase II (pol II) transcription of several different categories of genes, in the nucleus and thereby releases the stem-loop. This precursor of miRNA (pre-miRNA) is subsequently exported to the cytoplasm in an Exportin-5/RanGTPase-dependent manner and gets processed by the cytoplasmic RNase III Dicer into 21-23 nucleotides between miRNAs.

In addition, the present invention provides methods and compositions for knocking down the expression of a specific target gene by treating cells with the formulations comprising cationic lipid, a neutral colipid and a small RNA molecule. We demonstrate that our method delivers siRNA efficaciously into animal cells for the purpose of RNA interference. The area of medical science that is likely to benefit most from the present invention is RNAi therapeutics. The cationic lipid of the presently disclosed amphoteric pharmaceutical compositions is selected from the group consisting of N,N-di-n-tetradecyl,N-methyl-N-(2-guanidinyl)ethylammonium chloride, N,N-di-n-hexadecyl,N-methyl-N-(2-guanidinyl)ethylammonium chloride and N,N-di-n-octadecyl,N,N-di-(2-hydroxyethyl)ammonium chloride. The neutral colipid is selected from cholesterol, fatty alcohol, phosphatidyl ethanolamine, phosphatidyl choline, and sphingolipid or diacyl glycerol. The small RNA molecule that can be delivered into the cell cytoplasm with the help of the presently disclosed amphoteric pharmaceutical compositions is selected from siRNA, microRNA, antisense oligonucleotide or a decoy nucleotide. Two preferred cationic lipids are N,N-di-n-tetradecyl,N-methyl-N-(2-guanidinyl)ethylammonium chloride (lipid 1) for in vitro experiments and N,N-di-n-octadecyl,N-methyl-N-(2-guanidinyl)ethylammonium chloride (lipid 2) for in vivo experiments.

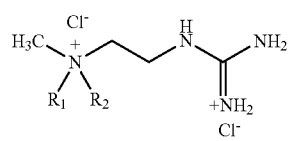

Lipid 1: R$_1$ = R$_2$ = n-C$_{14}$H$_{29}$
Lipid 2: R$_1$ = R$_2$ = n-C$_{16}$H$_{33}$
Lipid 3: R$_1$ = R$_2$ = n-C$_{18}$H$_{37}$ Although in the presently disclosed amphoteric liposomal formulation, the neutral colipid can be selected from cholesterol, fatty alcohol, phosphatidyl ethanolamine, phosphatidylcholine, sphingolipid or diacyl glycerol, a particularly preferred colipid is cholesterol. A preferred range of molar ratio of cationic lipid to co-lipid cholesterol is 1:1. Typically, the liposomes were prepared by dissolving the cationic lipid and the neutral co-lipid in the appropriate mole ratio in a mixture of methanol and chloroform in a glass vial. The solvent was removed with a thin flow of moisture free nitrogen gas and the dried lipid film was then kept under high vacuum for 8 h. The dried lipid film was hydrated in sterile deionized (RNAse free) water in a total volume of 1 ml at Guanidinylated cationic lipid concentration of 1 mM for a minimum of 12 h. Liposomes were vortexed for 1-2 minutes to remove any adhering lipid film and sonicated in a bath sonicator (ULTRAsonik 28X) for 2-3 minutes at room temperature to produce multilamellar vesicles (MLV). MLVs were then sonicated with a Ti-probe (using a Branson 450 sonifier at 100% duty cycle and 25 W output power) for 1-2 minutes to produce small unilamellar vesicles (SUVs) as indicated by the formation of a clear translucent solution.

In an embodiment of the present invention provides an in-vivo method for treating cancer in a warm-blooded animal, comprising administering a therapeutically effective animal, a therapeutically effective amount of the liposomal composition characterized in having small interfering RNAs (siRNAs) against Cdc20 (a key cell cycle regulator) useful for inhibiting tumour growth.

In an embodiment of the present invention provides the method comprising administering a composition comprising a cationic liposomes selected from the group comprising of small interfering ribonucleic acid (siRNA) or a plasmid DNA encoded short hairpin ribonucleic acid (shRNA) against Cdc20.

In an embodiment of the present invention provides the method wherein the liposomes have an average diameter in the range of 150-400 nm.

In an embodiment of the present invention provides the method wherein the siRNA against Cdc20 is encapsulated within the intravesicular space of the liposomes.

In an embodiment of the present invention provides the method wherein the shRNA against Cdc20 is electrostatically bound to the liposome.

In an embodiment of the present invention provides the method wherein the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, menangioma, neuroblastoma, and retinoblastoma colorectal adnoma, malignant melanoma, uveal melanoma, primitive neuroectodermal tumor, papillary carcinoma of the thyroid, alveolar rhabdomyosarcoma, plemorphic adenoma of salivary glands, sporadic typical lipomas, extraskeletal nyxoidchondrosarcoma, mucoepidemoid carcinoma, adenolymphoma of salivary gland, intraabdominal desmoplastic small round cell tumor, askins tumor, ethesioneuroblastoma, uterine leiomyomas, and myxoid liposarcoma.

In yet another embodiment the invention provides a Liposomal composition useful for inhibiting tumour growth comprising of encapsulated:
   a. Lipid,
   b. Co-lipid,
   c. characterized in having small interfering RNAs (siRNAs) against Cdc20 (a key cell cycle regulator),
   d. pharmaceutically acceptable carrier or diluents.

In yet another embodiment the invention provides the liposomal composition produced by
   (a) dissolving cationic lipids and co-lipid in chloroform and dried under a stream of $N_2$ gas;
   (b) vacuum dessicating the dried film of lipids and co-lipids for 6-12 h for removing residual organic solvent;
   (c) dissolving the vacuum-dessicated film of lipid and co-lipid in absolute ethanol and allowing ethanol solution to stand at 37° C. for 30 min;
   (d) dissolving the CDC20siRNA in RNA suspension buffer and allowing the resulting aqueous solution to stand at 37° C. for 30 min;
   (e) contacting the ethanol solution of the dried lipid film with the CDC20siRNA solution in RNA suspension buffer at 37° C. for 30 min;
   (f) diluting the resulting mixture with 300 mM NaCl and heating the mixture at 37° C. for 30 min;
   (g) removing the unentrapped CDC20siRNA by ultracentrifugation using 10 Kd size Amicon filter; and
   (h) diluting the liposomal solution containing entrapped CDC20siRNA with 5% aqueous glucose to cationic lipid concentration in the liposomal formulation.

In yet another embodiment the invention provides the composition wherein the lipid is selected from the group consisting of a guanidinylated cationic amphiphile with a stearyl tail, palmityl or a myristyl tail.

In yet another embodiment the invention provides the composition wherein the co lipid is selected from the group consisting of cholesterol, 1,2-dioleoyl-sn-glycero-3-phosphocholine (DOPC), aminopropyl polyethyleneglycol carbamyl-distearoylphosphatidyl-ethanolamine (DSPE-peg-$NH_2$).

In yet another embodiment the invention provides the composition wherein the RNA-interference is performed in a mammal.

In yet another embodiment the invention provides the composition in which the liposomes possess an average diameter in the range of 150-400 nm.

In yet another embodiment the invention provides the composition wherein the CDC20 siRNA encapsulated in liposomes is intravenously administered in C57BL/6J mice, significantly inhibits (by more than 4 fold) the growth of tumor nodules in lung tumor created by intravenous administration of B16F10 cells.

In yet another embodiment the invention provides the composition wherein the plasmid encoded CDC20 shRNA complexed to liposomes is administered intraperitoneally (i.p.), significantly inhibits (by more than 6 fold) the growth of solid B16F10 tumors in C57BL/6J mice.

In still another embodiment the invention provides a method for treating cancer in a warm-blooded animal, comprising administering a therapeutically effective animal, a therapeutically effective amount of the composition wherein said amount of a composition inhibits tumour growth.

In still another embodiment the invention provides the method comprising administering a composition comprising a cationic liposomes selected from the group comprising of small interfering ribonucleic acid (siRNA) or a plasmid DNA encoded short hairpin ribonucleic acid (shRNA) against CDC20.

In still another embodiment the invention provides the method wherein the liposomes have an average diameter in the range of 200-400 nm.

In still another embodiment the invention provides the method wherein the siRNA against CDC20 is encapsulated within the intravesicular space of the liposomes.

In still another embodiment the invention provides the method wherein the shRNA against CDC20 is electrostatically bound to the liposome.

In still another embodiment the invention provides the method wherein the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, menangioma, neuroblastoma, and retinoblastoma colorectal adnoma, malignant melanoma, uveal melanoma, primitive neuroectodermal tumor, papillary carcinoma of the thyroid, alveolar rhabdomyosarcoma, plemorphic adenoma of salivary glands, sporadic typical lipomas, extraskeletal nyxoidchondrosarcoma, mucoepidemoid carcinoma, adenolymphoma of salivary gland, intraabdominal desmoplastic small round cell tumor, askins tumor, ethesioneuroblastoma, uterine leiomyomas, and myxoid liposarcoma.

In still another embodiment the invention provides use of the composition for inhibiting tumour growth.

In a preferred embodiment, the animal cell such as the immortalized cell lines that can be procured from American Type Culture Collection (Bethesda) is maintained in tissue culture laboratory. Representative examples of such cells include COS-1 (African green monkey kidney cells), CHO (Chinese hamster ovary cells), HepG2 (human hepatocyte cells), RAW264.7 (mouse peritoneal macrophage cells) and the like.

In yet another embodiment, the cell can be either primary or secondary cell (i.e. the cells have been maintained in culture for short time after being isolated from the animal). Examples of primary cells include primary liver cells or primary muscle cells.

In a preferred embodiment, the presently disclosed invention provides the process for delivering small RNA molecules into the inside of animal cells. Such delivery process comprises of preparing a ternary complex of cationic lipid, colipid and the small RNA molecules, associating the ternary complexes with the cells and delivering the small RNA molecules into the interior of cells.

In yet another embodiment, the presently disclosed formulation can be used to deliver small RNA molecules into the cell cytoplasm for knocking down the expression of a specific target gene.

In a further embodiment, the cationic lipid can be used in combination with other neutral helper colipids such as cholesterol, phosphatidylethanolamine, phosphatidylglycerol, etc. The said therapeutic formulation may be stored at 0° C.-4° C. until complexed with the biologically active therapeutic molecules. Agents that prevent bacterial growth and increase the shelf life may be included along with reagents that stabilize the preparation, e.g., low concentrations of glycerol.

In one embodiment, the lipid: RNA mole ratios in the presently disclosed formulation can be varied within the range 1:1 to 100:1.

In one particularly preferred embodiment, the lipid: RNA mole ratio used in the presently disclosed formulation is 20:1.

In yet another preferred embodiment, the cationic lipid can be modified by attachment of functional groups such as a targeting signal or a level that facilitates intracellular delivery of small RNA molecules.

The lipid is considered cationic since the molecule bears an overall positive charge. The cationic lipid molecules described in the present invention are called amphoteric because the molecules contain hydrophilic groups (water loving groups) as well as hydrophobic (water hating) groups. Example of hydrophobic molecule includes hydrocarbons and the representative examples of the hydrophilic molecules include carbohydrates, peptides and compounds containing amines, amides, carboxylic acids, hydroxyl groups and the like. A siRNA is a nucleic acid containing 15-50 base pairs and preferably 21-25 base pairs, double stranded ribonucleic acid. The term nucleic acid, a commonly used term in the field of RNAi, refers to a polymer containing at least two nucleotides. Natural nucleotides in the art of the field contain deoxyribose (DNA) or ribose (RNA), a phosphate group, and an organic base such as purines or pyrimidines. Purines and pyrimidines further include natural compounds adenine, thymine, guanine, cytosine, uracils and their natural analogs. Nucleotides are the monomeric units of nucleic acid polymers which are linked together with the phosphate groups. A siRNA can be delivered into the interior of the cells with a view to produce a therapeutic benefit. Such delivery of genetic materials into our body cells for obtaining therapeutic effects is called gene therapy. Entry into the interior of cell cytoplasm is a requirement for knocking down the expression of the disease causing genes.

The present invention provides compositions for silencing expression of therapeutic genes in vitro by down regulation of mRNA and thus by down regulation of respective protein.

Sequences of the synthetic human Cdc20 siRNA (Seq ID No. 1 and 2)

```
sense:     5'r(CCACCAUGAUGUUCGGGUA) d(TT)3' antisense: 5'r(UACCCGAACAUCAUGGUGG) d(TG)3'
```

Sequences of the synthetic mouse Cdc20 siRNA (Seq ID No. 3 and 4)

```
sense:     5'r(AGUUCGUAUCAACCUUAAA) d(TT)3' antisense: 5'r(UUUAAGGAAGAUACGAACU) d(TG)3'
```

Cdc20 is an important cell cycle regulator required for the completion of mitosis in organisms from yeast to human. In the cell cycle, activation of the anaphase-promoting complex (APC) is a pre-requisite for anaphase initiation and for exit from mitosis. Cdc20 is one of the key regulators for APC; it binds and activates APC and the activated APC targets several mitotic regulators for degradation by ubiquitin-proteasome pathway. One of the major substrates of APC is the anaphase inhibitor securin. Before the onset of anaphase, securing binds to and inhibits separase, a ubiquitous protease. At the onset of anaphase, securin is degraded through ubiquitination by APC-Cdc20 complex and separase becomes free to cleave the components of the cohesion complex that holds the sister chromatids together at the metaphase of cell cycle. The pole ward force exerted on kinetochores then pulls the sister chromatids towards the opposite spindle poles. Since Cdc20 is highly expressed in several carcinomas, knockdown of the expression of Cdc20 through RNA interference holds therapeutic promise in combating cancer.

Guanidinylated cationic amphiphiles used in the present study for delivering siRNAs contain single guanidinium head-group and two aliphatic hydrocarbon chains and were synthesized as described previously [Sen, J, Chaudhuri, A. (2005). J Med Chem 48: 812-820.]. The sequences of the human and mouse Cdc20 siRNAs used are also shown. First we evaluated relative in vitro efficiencies of the cationic liposomes of lipid 1 and commercially available LipofectAmine2000 in delivering siRNA into cultured mammalian cells (CHO and RAW264.7) using a commercially available 19 bp fluorescein labeled non-silencing siRNA. Importantly, in both the cell lines, high degree of cellular uptake of the fluorescein labeled siRNA was observed when it was delivered in complexation with lipid 1. After confirming the non-silencing siRNA delivery efficacy of cationic guanidinylated lipid 1, we measured the efficiencies of the cationic liposomes of guanidinylated lipids 1-3 to down regulate the expression of reporter gene (GL2 luciferase) in both human lung carcinoma (A549) & mouse melanoma tumor (B16F10) using liposome bound GL2 luciferase siRNA. In both the cells, silencing effect on GL2 luciferase expression was found to be maximum when siRNA was delivered with the cationic liposomes of lipid 1. These findings prompted us next to evaluate the efficacies of lipid 1 in silencing the expression of Cdc20 at cellular level using a liposomally bound 19 bp Cdc20 siRNA at both protein and mRNA levels. The complex of 19 bp synthetic Cdc20 siRNA (25 nmol) and cationic liposomes of lipid 1 & equimolar amount of cholesterol (containing lipid:siRNA charge ratio of 14:1) was added to a single population of B16F10 cells synchronized at G1/S boundary (by double thymidine block). After 24 h of incubation, Western blot analysis of the cell lysate revealed essentially complete knockdown of Cdc20 protein expression. When cells were similarly treated with liposomally bound universal scrambled siRNA, expression of Cdc20 proteins was not inhibited. Consistent with these findings in the Western blot, the amount of Cdc20 mRNA in B16F10 cells treated with liposome: Cdc20 siRNA complex was found to be dramatically low compared to that in cells treated with siRNA: liposome complex of the universal scrambled siRNA.

Bio-distribution profile of the lipoplexes was evaluated using commercially available luciferase plasmid. While intravenous administration of the lipoplexes of lipids 1 & 2 failed to express luciferase in any organ under systemic settings, lipoplexes of lipid 3 showed 2-3 orders of magnitude higher luciferase transgene expression in mouse lung than in liver, spleen, kidney and heart. Such lung selective transfection efficiency of the lipoplex of lipid 3 prompted us to evaluate systemic potential of liposome encapsulated Cdc20 siRNA in combating melanoma lung metastasis. We used an established experimental lung metastasis model by intravenously injecting B16F10 murine melanoma cells stably transfected with luciferase reporter gene in C57BL/6J mice as described previously [Li, S D, Chono, S, Huang, L. (2008). Mol Ther, 16: 942-946]. Three consecutive doses of liposomal Cdc20 siRNA (5 μg siRNA per mouse per day) were intravenously administered on every alternate day from tenth day after intravenous injection of luciferase transduced B16F10 cells. Importantly, metastatic nodules were found to be significantly reduced in lung of mice treated with liposomally bound Cdc20 siRNA compared to the degree of metastatic lung nodule reduction in mice treated with liposomally bound universal scrambled siRNA or in mice treated with vehicle only. Consistent with such remarkably reduced metastatic lung nodules, the luciferase gene expression in the lung homogenate obtained from mice treated with liposomally encapsulated Cdc20 siRNA was significantly affected compared with that in mice treated with liposomally bound universal scrambled siRNA. Western Blot analysis of mice lung tumor homogenate confirmed significant reduction of Cdc20 expression in mice treated with liposomally bound Cdc20 siRNA relative to the degree of Cdc20 expression in mice treated with liposomally bound universal scrambled siRNA and vehicle alone Immunohistochemical staining with goat anti-mouse Cdc20 antibody and DAB as substrate also revealed widespread metastasis nodules across most of the lung tissue when mice were treated with vehicle alone or with liposomally bound universal scrambled siRNA compared to the number of metastasis nodules for mice treated with liposomally bound Cdc20 siRNA. The hematoxylin and eosin-stained tissue sections also showed presence of a few small metastatic nodules for mice treated with liposomally bound Cdc20 siRNA in contrast to widespread metastasis nodules across most of the lung when mice were administered with liposomally bound universal scrambled siRNA and vehicle alone.

Cdc20 siRNA: liposome complex increases the cell population at G2/M phase. Flow cytometric analysis for the Cyclin B1 content (marker for G2/M phase of cell cycle) confirmed the presence of significantly enhanced populations of G2/M phase for cells treated with liposomally bound Cdc20 siRNA.

The present invention will be explained in more detail in the following examples that are, however, not intended to limit the scope of the invention.

EXAMPLE 1

Syntheses of the cationic lipids 1-3 (FIG. 1). Lipids were synthesized following the procedures depicted schematically in FIG. 1.

Synthesis of Lipid 2.

Step-i. Synthesis of N,N-di-n-hexadecyl-N-[2-(N',N'-di-tertbutoxycarbonyl-guanidinyl]ethyl amine (III, FIG. 1). Mercuric chloride (0.28 g, 1.0 mmol) was added to a mixture of N-2-aminoethyl-N,N-di-n-hexadecylamine (I, 0.49 g. 0.95 mmol), bis-N-Boc-thiourea (II, 0.26 g, 0.95 mmol, prepared conventionally by reacting one equivalent of thiourea with 2 equivalents of BOC-anhydride in presence of 2 equivalents of sodium hydride in anhydrous tetrahydrofuran) and triethylamine (0.21 g, 2.1 mmol) dissolved in dry DMF (5 ml) and dry DCM (2 ml) at 0° C. with continuous stirring. The resulting mixture was stirred at 0° C. under nitrogen for 40 minutes, diluted with ethyl acetate (20 ml) and filtered through a pad of celite. The filtrate was sequentially washed with water (2×20 ml) and brine solution (2×20 ml), dried over anhydrous sodium sulfate, filtered and the solvent from the filtrate removed by rotary evaporation. The residue upon column chromatographic purification with 60-120 mesh silica gel using 2-2.5% methanol-dichloromethane (v/v) as eluent afforded 0.51 g of the pure title compound III (71%, Rf=0.8, 10% methanol-dichloromethane, v/v).

1H NMR (200 MHz, CDCl3): /ppm=0.9 [t, 6H, CH3-(CH2)13-]; 1.2-1.4 [bs, 56H, —(CH2)14-]; 1.4-1.6 [2s, 18H, —CO—O—C(CH3)3]; 2.4-2.7 [bm, 6H, —N(—CH2-CH2-)2-; —N—CH2-CH2-NH—]; 3.4-3.6 [m, 2H, —N—CH2-CH2-NH—]; 8.6 [t, 1H, —CH2-NH—]; 11.4 [s, 1H, —NHBOC].

Step-ii. Synthesis of N,N-di-n-hexadecyl-N-[2-(N',N'-di-tertbutoxycarbonyl-guanidinyl]ethyl-N-methylammonium iodide (FIG. 1). The intermediate III obtained above in step i was dissolved in 3 ml dichloromethane/methanol (2:1, v/v) and 3 ml methyl iodide was added. The solution was stirred at room temperature overnight. Solvent was removed on a rotary evaporator. The residue upon column chromatographic purification with 60-120 mesh size silica gel and 3% methanol in dichloromethane (v/v) as eluent afforded 0.47 g of the title compound (78% yield, Rf=0.6, 10% methanol in dichloromethane, v/v).

1H NMR (200 MHz, CDCl3): /ppm=0.9 [t, 6H, CH3-(CH2)14-]; 1.2-1.3 [m, 52H, —CH3(CH2)13-]; 1.4-1.6 [2s, 18H, —CO—O—C(CH3)3]; 1.65 [m, 4H, —N+(—CH2-CH2-)2]; 3.3 [s, 3H, —N+—CH3]; 3.4 [m, 4H, —N+(—CH2-CH2-)2]; 3.6 [m, 2H, —N+—CH2-CH2-NH—]; 3.8 [m, 2H, —N+—CH2-CH2-NH—]; 8.4 [t, 1H, —CH2-NH—]; 11.3 [s, 1H, —NHBOC].

Steps-iii & iv. Synthesis of N, N-di-n-hexadecyl-N-[2-guanidinyl]ethyl-N-methylammonium chloride (Lipid 2, FIG. 1).

The intermediate obtained above in step ii was dissolved in dry DCM (2 mL) and TFA (2 ml) was added to the solution at 0° C. The resulting solution was left stirred at room temperature overnight to ensure complete deprotection. Excess TFA was removed by flushing nitrogen to give the title compound as a trifluoroacetate salt. Column chromatographic purification using 60-120 mesh size silica gel and 12-14% (v/v) methanol-chloroform as eluent followed by chloride ion exchange chromatography over amberlyst A-26 chloride ion exchange resin afforded 0.31 g of the pure lipid B (94% yield, Rf=0.3, 10% methanol in chloroform, v/v).

1H NMR (200 MHz, CDCl3): /ppm=0.9 [t, 6H, CH3-(CH2)14-]; 1.2-1.3 [m, 52H, —CH3(CH2)13-]; 1.5-1.7 [m, 4H, —N+(—CH2-CH2-)2]; 3.0 [s, 3H, —N+—CH3]; 3.1 [m, 4H, —N+(—CH2-CH2-)2]; 3.5 [m, 2H, —N+—CH2-CH2-NH—]; 3.7 [m, 2H, —N+—CH2-CH2-NH—]; 7.4[bs, 4H, —NH2+]; 8.7 [bs, 1H, —CH2-NH].

LSIMS (lipid 2): m/z: 565 [M+] (calcd for C36H77N4, 22%).

EXAMPLE 2

Figure 2:
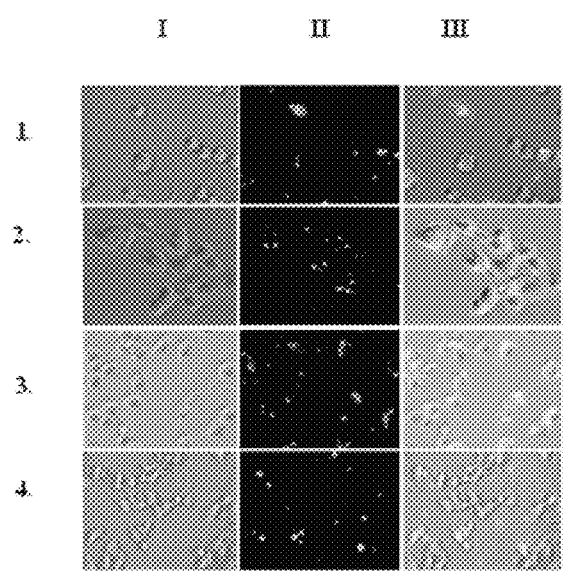
FIG. 2 shows cellular uptake of liposomally bound fluorescent non-silencing siRNA in four different cell lines. Inverted fluorescence micrographs of the CHO (1), COS-1 (2), RAW264.7 (3) and HepG2 (4) cells transfected with complex of fluorescein labeled siRNA, & cationic liposomes prepared with lipid 1. I. phase contrast bright field image; II. Fluorescence micrograph and III. Overlay images. (Magnification: 20×).

Evaluation of siRNA delivery defficacies of the ampho-teric composition containing lipid 1, (FIG. 1) in four cells including COS-1, RAW264.7, CHO and HepG2 cells (FIG. 2).

Preparation of Liposomes for In Vitro Experiments:
Cationic lipids taken in methanol and cholesterol (in 1:1 molar ratio) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

Method.

Cells were seeded at a density of 40,000 cells/well in a 24-well plate for 18 h before transfection in 500 µl of growth medium such that the well became 30-50% confluent at the time of transfection. For each well to be transfected, siRNA duplex-Liposome complexes were prepared as follows:

a). 20 pmol fluorescently labeled siRNA duplex namely, Control (non-sil) siRNA, Fluorescein (Catalog No. 1022079, QIAGEN, USA) was diluted in 50 µL Opti-MEMO I Medium without serum in the well of the tissue culture plate and was mixed gently.

b). Liposomes prepared using equimolar cationic lipid B and cholesterol was mixed gently before use. 1 µl liposome was then added to each well containing the diluted siRNA molecules, mixed gently and was incubated for 10-20 minutes at room temperature.

The siRNA duplex-Liposome complexes obtained above were added to each well containing 40,000 cells. After incubation of the cell plates in a humidified atmosphere containing 5% CO2 at 37° C. for 4 h, 200 µl of growth medium containing 10% FBS (CM1X) were added to cells. After 8 h, the medium was removed completely from the wells and cells were washed with PBS (200 µl). PBS was discarded and micrographs were taken on fresh PBS (200 µl). The fluorescently labeled cells were observed under an inverted fluorescence microscope (Nikon, Japan).

EXAMPLE 3

Figure 3:
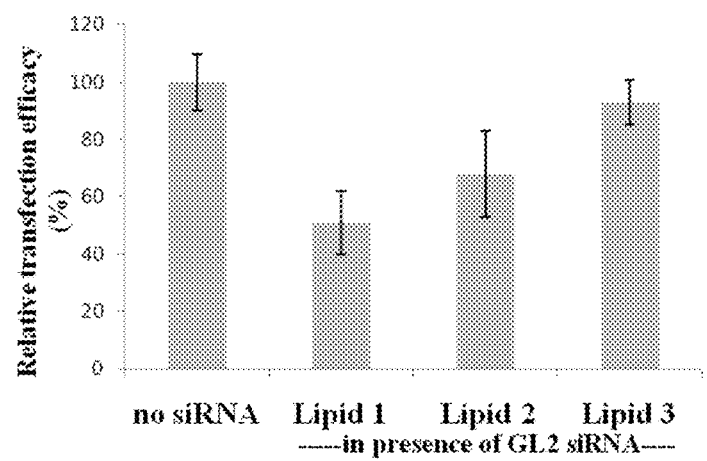
FIG. 3 shows luciferase gene silencing study by liposomally bound GL2 siRNA. Knock down of firefly luciferase GL2 gene expression in A549 (a) and B16F10 cells (b) by delivering luciferase GL2 siRNA encapsulated in cationic liposomes of lipids 1-3.
Figure 3:
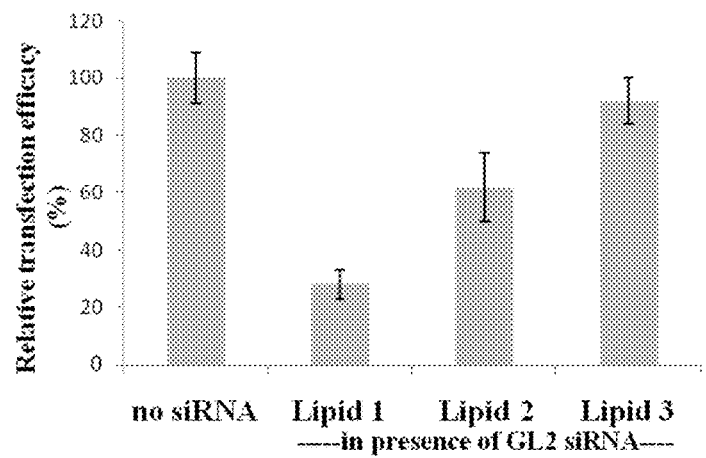

Knocking down the expression of firefly luciferase GL2 gene in A549 & B16F10 cells by delivering luciferase GL2 siRNA with the formulation containing equimolar amounts of Lipid 1 (FIG. 1) and cholesterol (FIG. 3).

Preparation of Liposomes for In Vitro Experiments:
Cationic lipids taken in methanol and cholesterol (in 1:1 molar ratio) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

One day before transfection, cells were seeded at 1×104 cells/well in 96-well plates with 100 µL of growth medium containing 10% FBS medium and incubated for 24 h. Cells were 50-60% confluent before transfection. The complex of luciferase GL2 siRNA, liposome and pCMV-GL2 Luciferase plasmid (obtained as a generous gift from the laboratory of Professor Leaf Huang, University of North Carolina, Chapel Hills, USA) was prepared as follows:

a. 5-50 pmol luciferase GL2 siRNA duplex was diluted in 25 µL Opti-MEMO I Reduced Serum Medium without serum and was mixed gently.

b. Liposomes prepared using equimolar cationic lipid A and cholesterol was mixed gently before use. 1.38 µl of liposome (containing 1 mM cationic lipid A) was then diluted with 115 µl of Opti-MEMO I Reduced Serum Medium and mixed gently.

c. Diluted siRNA duplex was added to the diluted liposome and mixed gently. 0.9 µg of the pCMV-GL2Luciferase plasmid (9 µl of 0.1 µg/µl stock plasmid) was added to the siRNA-liposome conjugate and incubated for 10-20 minutes at room temperature. This gave a final volume of 150 µl siRNA duplex-liposome-plasmid DNA complex.

d. 50 µl of the siRNA duplex-liposome-plasmid DNA complex prepared above was added to each well. Medium was changed after 4 h and the cells were incubated for 30 hours at 37° C. in a CO2 incubator and assayed for knock-down of luciferase expression. Each gene knock-down experiment with siRNA was done in triplicate using Microplate Luminometer (FLx800, Bio-Tek Instruments, USA).

EXAMPLE 4

Figure 4:
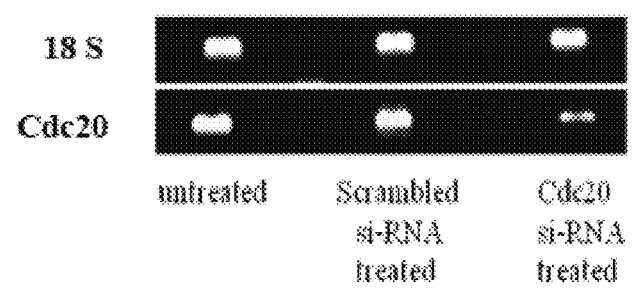
FIG. 4 shows down regulation of mRNA level in A549 cell when treated with liposomally bound human Cdc20 siRNA. Suppression of Cdc20 expression at mRNA level by transfecting cells with Cdc20 siRNA. A549 Cells were synchronized at the G1/S boundary by a double thymidine block. After 36 h thymidine block, the cells were released from the arrest and transfected with human Cdc20 siRNA in complexation with cationic liposomes of lipid 1 (right lane) and with universal scrambled siRNA encapsulated in cationic liposomes of lipid 1 (middle lane). Untreated cells were used as another control (left lane). After 24 h, mRNAs were extracted from all the cells, cDNA was synthesized by Reverse Transcription reaction and amplified by Polymerase Chain Reaction and finally resolved in 2% agarose gel.
Figure 5:
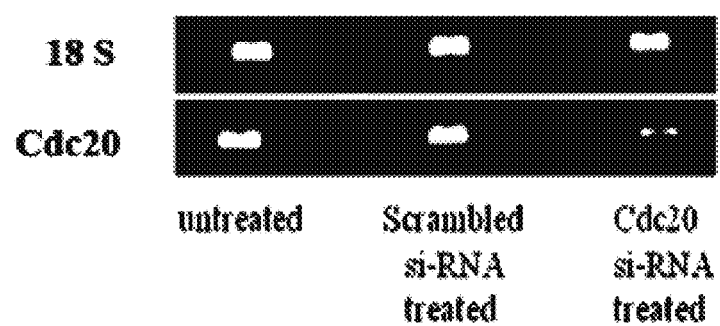
FIG. 5 shows down regulation of mRNA level in B16F10 cell when treated with liposomally bound mouse Cdc20 siRNA. Suppression of Cdc20 expression at mRNA level by transfecting cells with Cdc20 siRNA. B16F10 cells were synchronized at the G1/S boundary by a double thymidine block. After 36 h thymidine block, the cells were released from the arrest and transfected with mouse Cdc20 siRNA in complexation with cationic liposomes of lipid 1 (right lane) and with universal scrambled siRNA encapsulated in cationic liposomes of lipid 1 (middle lane). Untreated cells were used as another control (left lane). After 24 h, mRNAs were extracted from all the cells, cDNA was synthesized by Reverse Transcription reaction and amplified by Polymerase Chain Reaction and finally resolved in 2% agarose gel.

Down regulation of Cdc20 mRNA (FIG. 4 and FIG. 5).
Preparation of Liposomes:
Cationic lipid 1 taken in methanol and cholesterol (in 1:1 molar ratio) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

Cell Culture:
A549 (Human lung adenocarcinoma epithelial cell line) and B16F10 cells (Murine Melanoma Cells) were procured from ATCC vide catalogue no. ATCC-CCL-185 and ATCC-cr1-6475 respectively. Cells were cultured in DMEM medium (Sigma) containing 10% fetal bovine serum (South American Origin, Gibco, USA) and 1% penicillin-streptomycin-kanamycin at 37° C. in a humidified atmosphere of 5% $CO_2$ in air.

Method:
Cells were first synchronized by double thymidine block to block cells at the G1/S boundary and then grown in fresh medium. After 2 h of addition of fresh medium to cells synchronized at G1/S boundary, the cells (approximately $1 \times 10^6$ cells per flask) were treated with lipoplexes containing 25 nmol of Cdc siRNA (or 25 nmol control scrambled siRNA) at a 14:1 charge ratio of lipid:siRNA. After 4 h of incubation, fresh medium was added to it. After 24 h of incubation, the total RNAs were extracted from the cells by dissolving in 1 mL Trizol solution (Invitrogen). First-Strand cDNAs were synthesized from the corresponding mRNAs by Reverse Transcription reaction according to the manufacturer's protocol (Reverse Transcription System, Promega, USA). cDNAs were amplified using forward (Seq ID No. 5) (5'-TCCAAGGTTCAGACCACTCC-3') and reverse (Seq ID No. 6) (5'-GATCCAGGCCACAGAGGATA-3') primers for Cdc20 by Polymerase chain reaction using PCR master mix (Promega, USA). 18S was used as the internal control for PCR. Finally, the amplified DNAs were resolved in 2% agarose gel.

Result:
The prior findings prompted us next to evaluate the efficacies of lipid 1 in silencing the expression of Cdc20 using a liposomally bound 19 bp Cdc20 siRNA at mRNA levels. The complex of 19 bp synthetic Cdc20 siRNA (25 nmol) and cationic liposomes of lipid 1 & equimolar amount of cholesterol (containing lipid: siRNA charge ratio of 14:1) was added to a single population of B16F10 and A549 cells synchronized at G1/S boundary (by double thymidine block). After 24 h of incubation, RT-PCR analysis was performed. The amount of Cdc20 mRNA in B16F10 and A549 cells treated with liposome: Cdc20 siRNA complex was found to be dramatically low compared to that in cells treated with siRNA:liposome complex of the universal scrambled siRNA.

EXAMPLE 5

Figure 6:
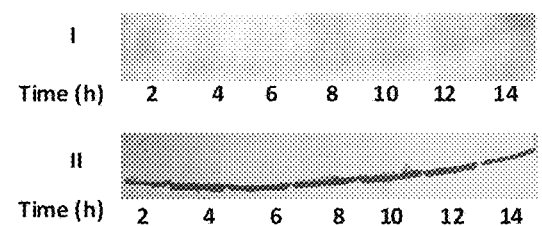
FIG. 6 shows down regulation of protein level in A549 cell when treated with liposomally bound human Cdc20 siRNA. Suppression of Cdc20 protein expression. A549 cells were synchronized at the G1/S boundary by a double thymidine block. After 36 h thymidine block, the cells were released from the arrest and were transfected with human Cdc20 siRNA in complexation with cationic liposomes of lipid 1 (I) and with universal scrambled siRNA in complexation with cationic liposomes of lipid 1 (II) as control and another set left untreated as another control (III). 48 h after transfection, cells were lysed and levels of Cdc20 were determined by immunoblotting.
Figure 7:
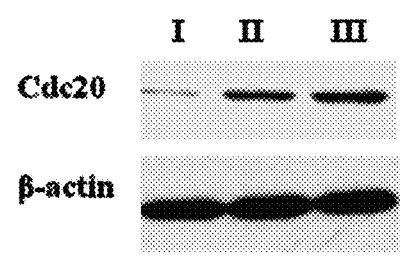
FIG. 7 shows down regulation of protein level in B16F10 cell when treated with liposomally bound human Cdc20 siRNA. Suppression of Cdc20 protein expression. B16F10 cells were synchronized at the G1/S boundary by a double thymidine block. After 36 h thymidine block, the cells were released from the arrest and were transfected with mouse Cdc20 siRNA in complexation with cationic liposomes of lipid 1 (I) and with universal scrambled siRNA in complexation with cationic liposomes of lipid 1 (II) as control and another set left untreated as another control (III). 48 h after transfection, cells were lysed and levels of Cdc20 were determined by immunoblotting.

Down regulation of Cdc20 protein (FIG. 6 and FIG. 7).
Preparation of Liposomes:
Cationic lipid 1 taken in methanol and cholesterol (in 1:1 molar ratio) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

Cell Culture:
A549 (Human lung adenocarcinoma epithelial cell line) and B16F10 cells (Murine Melanoma Cells) were procured from ATCC vide catalogue no. ATCC-CCL-185 and ATCC-cr1-6475 respectively. Cells were cultured in DMEM medium (Sigma) containing 10% fetal bovine serum (South American Origin, Gibco, USA) and 1% penicillin-streptomycin-kanamycin at 37° C. in a humidified atmosphere of 5% $CO_2$ in air.

Method:
Cells were synchronized with a double thymidine block. Briefly, cells were grown in the presence of 2 mM thymidine (Sigma) for 18 h, washed with PBS, sub-cultured and grown in fresh medium without thymidine for 8 h. Cells were then incubated with 2 mM thymidine for 18 h to block cells at the G1/S boundary and then grown in fresh medium. After 2 h of addition of fresh medium, the cells (approximately $1 \times 10^6$ cells per flask) were treated with lipoplexes containing 25 nmol of Cdc20 siRNA (or 25 nmol control scrambled siRNA) at a lipid:siRNA charge ratio of 14:1. After 4 h of incubation, the fresh medium was added to it. After 48 h, the cells were detached from the flask using a cell scrapper. Whole cell lysates were prepared by lysing the cells. Total protein content in each sample was determined by BCA method. Cell lysates were loaded and separated on a 7.5% polyacrylamide gel electrophoresis. Proteins were transferred onto a nitrocellulose membrane (Hybond-C extra, Amersham Biosciences, NJ) using wet blotting. Membrane was blocked for 1.5 h with 3% BSA solution in PBS-T (phosphate buffer saline containing 0.05% Tween-20). Blot was then incubated with polyclonal antibody raised against Cdc20 of human origin in rabbit (Chemicon International) at 1:500 dilution for overnight at 4° C. After washing three times with PBS-T, the membrane was incubated with goat anti-rabbit secondary antibody conjugated to horseradish peroxidase (Bangalore Genei, India) at 1:1000 dilutions for 60 min. After washing three times with PBS-T, protein bands were visualized using TMB-Blotting methods with TMB (Pierec Biotechnology Inc, Pittsburgh, Pa.) according to the manufacturer's protocol.

Result:
The prior findings prompted us next to evaluate the efficacies of lipid 1 in silencing the expression of Cdc20 at cellular level using a liposomally bound 19 bp Cdc20 siRNA at protein levels. The complex of 19 bp synthetic Cdc20 siRNA (25 nmol) and cationic liposomes of lipid 1 & equimolar amount of cholesterol (containing lipid:siRNA charge ratio of 14:1) was added to a single population of B16F10 and A549 cells synchronized at G1/S boundary (by double thymidine block). After 24 h of incubation, Western blot analysis of the cell lysate revealed knockdown of Cdc20 protein expression. When cells were similarly treated with liposomally bound universal scrambled siRNA, expression of Cdc20 proteins was not inhibited.

EXAMPLE 6

Figure 8:
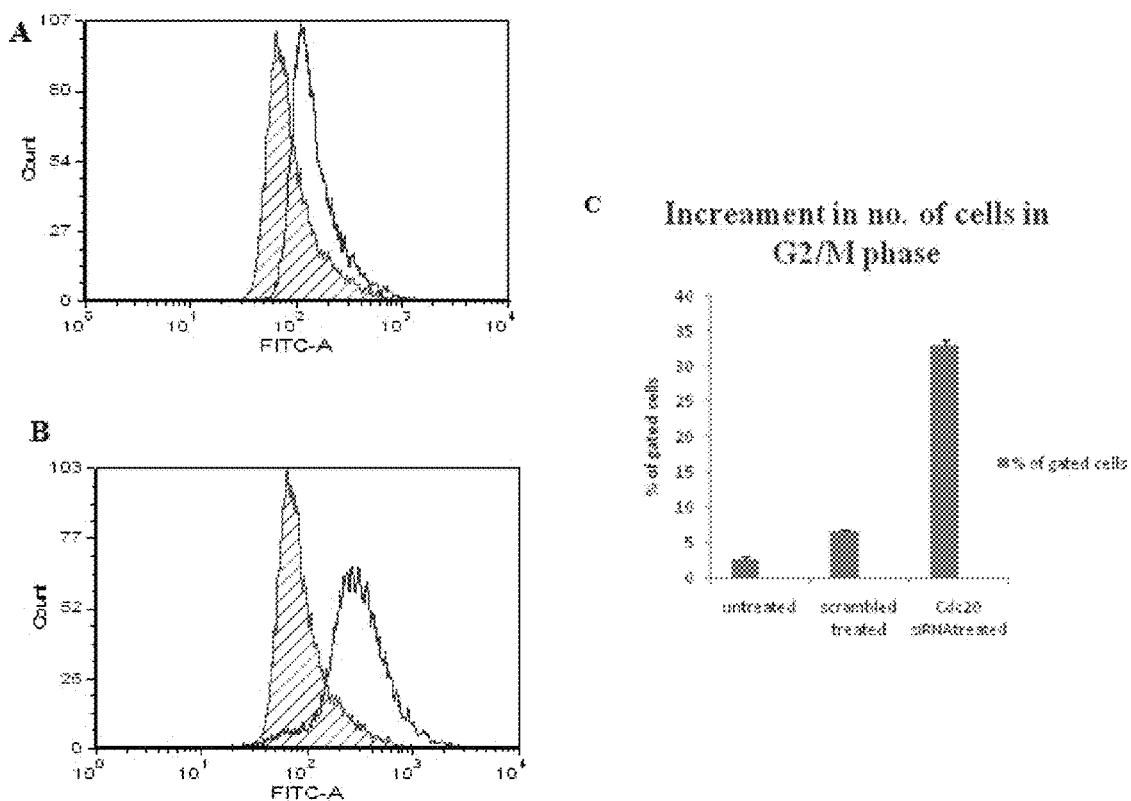
FIG. 8 shows Flow Cytometric analysis for the Cyclin B1 content (marker for G2/M phase of cell cycle) in A549 cell when treated with liposomally bound human Cdc20 siRNA. Transfection of A549 cells with liposomally associated Cdc20 siRNA leads to enhanced population of cells in G2/M phase. A549 cells were synchronized at the G1/S boundary by a double thymidine block and cells were released from the arrest. Cells were then transfected with Cdc20 siRNA encapsulated in the cationic liposomes of lipid 1 and with universal scrambled siRNA encapsulated in the cationic liposomes of lipid 1. Untreated cells were used as the control cells in both the cases. After 24 h, cells were trypsinized, fixed, permeabilized, incubated with primary antibody of Cyciln B1 (a marker of G2/M phase) followed by incubation with (FITC) conjugated secondary antibody and finally analyzed by flow cytometry. (a) shows overlap of FACS profiles for the Cyclin B1 for cells treated with liposome associated universally scrambled si-RNA and that for untreated cells. (b) Shows the corresponding Cyclin B1 profiles for Cdc20 siRNA treated cells and that for the untreated control cells. (c) Shows the enhanced populations G2/M phase for cells treated with liposomally bound Cdc20 siRNA.
Figure 9:
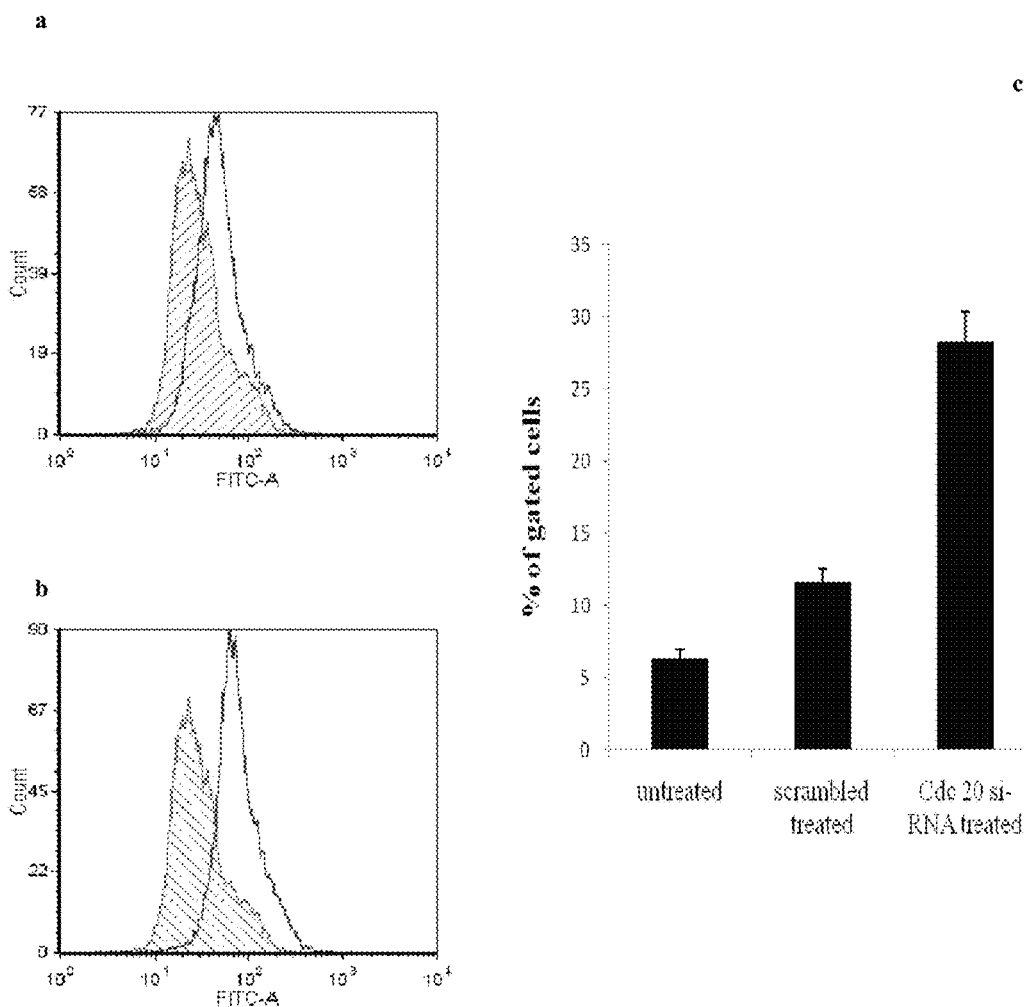
FIG. 9 shows Flow Cytometric analysis for the Cyclin B1 content (marker for G2/M phase of cell cycle) in B16F10 cell when treated with liposomally bound mouse Cdc20 siRNA. Transfection of B16F10 cells with liposomally associated Cdc20 siRNA leads to enhanced population of cells in G2/M phase. B16F10 cells were synchronized at the G1/S boundary by a double thymidine block and cells were released from the arrest. Cells were then transfected with Cdc20 siRNA encapsulated in the cationic liposomes of lipid 1 and with universal scrambled siRNA encapsulated in the cationic liposomes of lipid 1. Untreated cells were used as the control cells in both the cases. After 24 h, cells were trypsinized, fixed, permeabilized, incubated with primary antibody of Cyciln B1 (a marker of G2/M phase) followed by incubation with (FITC) conjugated secondary antibody and finally analyzed by flow cytometry. (a) shows overlap of FACS profiles for the Cyclin B1 for cells treated with liposome associated universally scrambled si-RNA and that for untreated cells. (b) shows the corresponding Cyclin B1 profiles for Cdc20 siRNA treated cells and that for the untreated control cells. (c) shows the enhanced populations G2/M phase for cells treated with liposomally bound Cdc20 siRNA.

Transfection of A549 and B16F10 cells with liposomally associated Cdc20 siRNA leads to enhanced population of cells in G2/M phase (FIG. 8 and FIG. 9).

Preparation of Liposomes:

Cationic lipid 1 taken in methanol and cholesterol (in 1:1 molar ratio) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

Cell Culture:

A549 (Human lung adenocarcinoma epithelial cell line) and B16F10 cells (Murine Melanoma Cells) were procured from ATCC vide catalogue no. ATCC-CCL-185 and ATCC-crl-6475 respectively. Cells were cultured in DMEM medium (Sigma) containing 10% fetal bovine serum (South American Origin, Gibco, USA) and 1% penicillin-streptomycin-kanamycin at 37° C. in a humidified atmosphere of 5% $CO_2$ in air.

Method:

Cells were synchronized with a double thymidine block. Cells were grown in the presence of 2 mM thymidine (Sigma) for 18 h, washed with PBS, subcultured and grown in fresh medium without thymidine for 8 h. Cells were then incubated with 2 mM thymidine for 18 h to block cells at the G1/S boundary and then grown in fresh medium. After 2 h of addition of fresh medium, the cells (approximately $1 \times 10^6$ cells per flask) were treated with lipoplexes containing 25 nmol of siRNA and at a charge ratio lipid:siRNA 14:1. After 4 h of incubation, the fresh medium was added to it. After 24 h of incubation, cells were detached from the flask by tripsinization, fixed by 2% paraformaldehyde in PBS, permeabilized by 0.1% Triton-X 100 in PBS and pelleted. 1 µg of primary antibody to Cyclin B1 (a marker of G2/M phase of cell cycle) in 250 µL of PBS was added to the cell pellets followed by vortexing and incubation for 15-30 min in a covered ice-bucket. Supernatant was aspirated and 250 µL of PBS was added to each pellet. Then 1 µg of (FITC)-conjugated secondary antibody was added to each pellet followed by vortexing and incubation for 15-30 min in a covered ice-bucket. Supernatant was aspirated and the pellets were resuspended in 5000 µL of PBS and analyzed by FACS.

Result:

Flow cytometric analysis for the Cyclin B1 content (marker for G2/M phase of cell cycle) confirmed the presence of significantly enhanced populations of G2/M phase for cells treated with liposomally bound Cdc20 siRNA. Relative FACS profiles for the Cyclin B1 (a marker for the G2/M phase of cell cycle) in B16F10 and A549 cells treated with liposomally associated Cdc20 siRNA with those for B16F10 and A549 cells treated with control universally scrambled siRNA and untreated B16F10 and A549 cells revealed significantly enhanced populations of G2/M phase for cells treated with liposomally bound Cdc20 siRNA.

EXAMPLE 7

Solid tumor growth inhibition study of Cdc20 shRNAs (FIG. 10):

Preparation of Liposomes:

Cationic lipid 3 taken in methanol and cholesterol, DOPC, DSPE-PEG-$NH_2$ (molar ratio 1:1:1:0.05) taken in chloroform were dried under a stream of $N_2$ gas and vacuum-dessicated for a minimum of 6 h to remove residual organic solvent. The dried lipid film was hydrated in RNAse free water at cationic lipid concentration of 1 mM, for a minimum of 12 h. Liposomes were vortexed to remove any adhering lipid film and probe sonicated until a clear translucent solution formed.

Cell Culture:

A549 (Human lung adenocarcinoma epithelial cell line) and B16F10 cells (Murine Melanoma Cells) were procured from ATCC vide catalogue no. ATCC-CCL-185 and ATCC-crl-6475 respectively. Cells were cultured in DMEM medium (Sigma) containing 10% fetal bovine serum (South American Origin, Gibco, USA) and 1% penicillin-streptomycin-kanamycin at 37° C. in a humidified atmosphere of 5% $CO_2$ in air.

Method:

6-8 weeks old female C57BL/6J mice (each weighing 20-22 g) with aggressive B16F10 tumors (produced by subcutaneous injections of $1.5 \times 10^5$ B16F10 cells in 100 µL Hank's buffer salt solution (HBSS) into the left flanks on day 0) were randomly sorted into two groups and each group (n=5) was administered intraperitoneally with Lipid 3:DOPC:Chol:DSPE-PEG-$NH_2$ (0.5:1:1:0.05): Cdc20 shRNAs (50 µg) complex in 5% aqueous glucose, Lipid 3:DOPC:Chol:DSPE-PEG-$NH_2$ (1:1:1:0.05): pCMV-β-gal (50 µg) complex in 5% aqueous glucose and 5% aqueous glucose alone on day 15, 17, 19, 21 and 23. Tumor volumes ($V=1/2.ab^2$ where, a=maximum length of the tumor and b=minimum length of the tumor measured perpendicular to each other) were measured with a slide calipers for up to 23 days. Results represent the means+/−SD (for n=3 tumors).

Result:

Remarkable inhibition of tumor growth was achieved only when the Cdc20 shRNA was administered in complexation with the above mentioned liposome. Similarly, no significant inhibition of tumor growth was observed when liposome complexed with pCMV-β-gal in 5% aqueous glucose was administered. Mice administered with vehicle alone (5% aqueous glucose solution) developed large tumor on day 23 and were sacrificed at that point.

EXAMPLE 8

Figure 11:
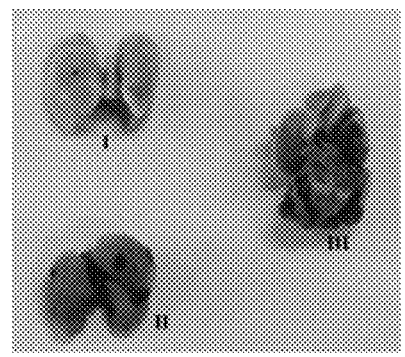
FIG. 11 shows images of lungs excised from the tumor-bearing mice on day 17 after three consecutive treatments of liposomally encapsulated Cdc20 siRNA in C57BL/6J mice. a. Images of lungs excised from the tumor-bearing mice on day 17 after three consecutive treatments. I. tumors treated with cationic liposomes of Lipid 3: Cdc20 siRNAcomplexes; II. tumors treated cationic liposomes made of Lipid 3: universal scrambled siRNA (as control) and III. tumors treated with vehicle (5% aqueous glucose) only. b. Luciferase activity in the tumor-loaded lungs on day 15 after three consecutive intravenous (i.v.) injections of Cdc20 siRNA in different formulations on days 10, 12 and 14. n=5. *P<0.01 as compared to the siRNA in 5% glucose. c. Western blot of the mice lung tumor homogenate. Lane. I. mice treated with cationic liposomes made of Lipid 3: cdc20 siRNAcomplexes; II. mice treated cationic liposomes made of Lipid 3: universal scrambled siRNA (as control) and III. mice treated with vehicle (5% aqueous glucose) only.
Figure 11:
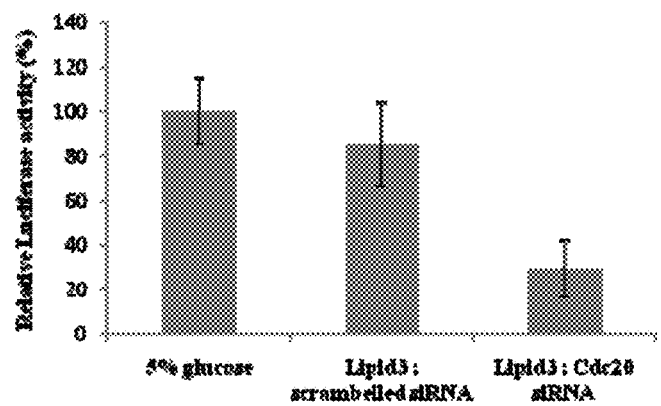
Figure 11:
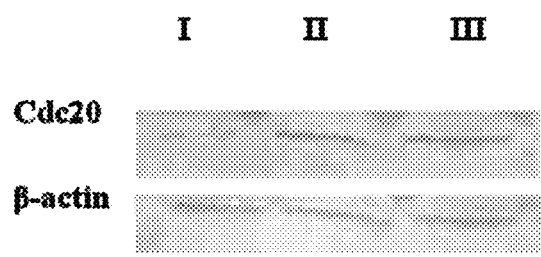
Figure 12:
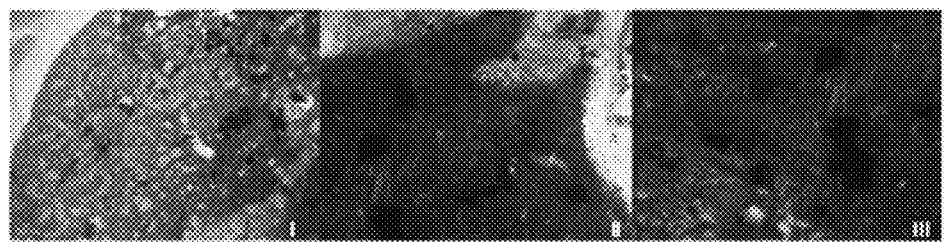
FIG. 12 shows immunohistochemical staining and hematoxylin & eosin staining of the lung tissue sections for C57BL/6J mice treated with liposomally encapsulated Cdc20 siRNA. a. Immunohistochemical staining of the lung tissue sections for mice treated with various cationic liposome:siRNA complexes using goat anti mouse Cdc20 antibody and DAB as substrate. I: representative lung tissue section in mice treated with liposomally bound Cdc20 siRNA; II: representative lung tissue section in mice treated with liposomally bound universally scrambled siRNA and III: representative lung tissue section in mice treated with 5% glucose only (original magnification×40). b. Hematoxylin and eosin-stained tissue sections for mice treated with various cationic liposome: siRNA complexes. I: representative lung tissue section in mice treated with liposomally bound Cdc20 siRNA; II: representative lung tissue section in mice treated with liposomally bound universally scrambled siRNA and III: representative lung tissue section in mice treated with 5% glucose only (original magnification×40).
Figure 12:
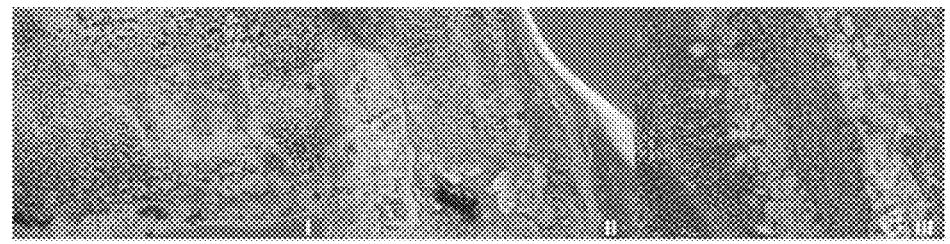

Inhibition of melanoma growth on lung by guanidinylated cationic liposome-Cdc20 siRNA complex (FIG. 11).

Preparation of Liposome-siRNA Complexes:

siRNA was encapsulated inside the liposome by SNALP method (Jeffs L B, et al. (2005) Pharmaceutical Research, 22:362-372). Briefly, cationic lipids and cholesterol (in 1:1 molar ratio) taken in chloroform were dried under a stream of $N_2$ gas and vacuum-dessicated for a minimum of 6 h to remove residual organic solvent. The dried lipid mixture was dissolved in absolute ethanol. siRNA was diluted in RNA suspension buffer. These two solutions were heated to 37° C. prior to vesicle formation. The siRNA solution was added to the lipid solution resulting in the spontaneous formation of a liposomal suspension containing approximately 45% ethanol. The mixture was kept at 37° C. for 30 min, diluted with 300 mM NaCl heated to 37° C. and kept at 37° C. for 30 min.

The mixture was transferred to an Amicon Ultra (10 Kd) and the untrapped siRNAs and ethanol were removed by centrifugation. The solution was diluted with 5% glucose to a final lipid concentration of 5 mM.

Cell Culture:

B16F10 cells (Murine Melanoma Cells) were procured from ATCC vide catalogue no. ATCC-crl-6475. Cells were cultured in DMEM medium (Sigma) containing 10% fetal bovine serum (South American Origin, Gibco, USA) and 1% penicillin-streptomycin-kanamycin at 37° C. in a humidified atmosphere of 5% $CO_2$ in air.

Method:

Murine model of lung metastasis was established by intravenously injecting $2 \times 10^5$ B16F10 cells into C57BL/6J mice. Metastatic melanoma tumor-bearing mice were intravenously injected with lipid 3: Cdc20 siRNA complexes on day 10, 12 and 14 post B16F10 injection. Universally scrambled siRNA encapsulated in liposomes of lipid 3 was also administered as a negative control. On day 17, the mice were killed and the tumor-loaded lungs were removed. One lobe of each lung was analyzed for luciferase activity in order to quantify the lung metastasis nodules. The lobe was homogenized in 400 μL of lysis buffer (2 mM EDTA and 0.2% Triton X-100, pH 7.8 in 0.1 MTris-HCl) followed by centrifugation at 10,000 rpm for 10 min at 4° C. 10 μL of the supernatant was mixed with 50 μL of luciferase substrate (Luciferase Assay System; Promega, Madison, Wis.), and the luciferase activity was measured using a plate reader FLx800 microplate luminescence reader (Bio-Tek instruments, INC, UK).

Result:

Bio-distribution profile of the lipoplexes was evaluated using commercially available luciferase plasmid. While intravenous administration of the lipoplexes of lipids 1 & 2 failed to express luciferase in any organ under systemic settings, lipoplexes of lipid 3 showed 2-3 orders of magnitude higher luciferase transgene expression in mouse lung than in liver, spleen, kidney and heart. Such lung selective transfection efficiency of the lipoplex of lipid 3 prompted us to evaluate systemic potential of liposome encapsulated Cdc20 siRNA in combating melanoma lung metastasis. We used an established experimental lung metastasis model by intravenously injecting B16F10 murine melanoma cells stably transfected with luciferase reporter gene in C57BL/6J mice as described previously. Three consecutive doses of liposomal Cdc20 siRNA (5 μg siRNA per mouse per day) were intravenously administered on every alternate day from tenth day after intravenous injection of luciferase transduced B16F10 cells. Importantly, metastatic nodules were found to be significantly reduced in lung of mice treated with liposomally bound Cdc20 siRNA compared to the degree of metastatic lung nodule reduction in mice treated with liposomally bound universal scrambled siRNA or in mice treated with vehicle only. Consistent with such remarkably reduced metastatic lung nodules, the luciferase gene expression in the lung homogenate obtained from mice treated with liposomally encapsulated Cdc20 siRNA was significantly affected compared with that in mice treated with liposomally bound universal scrambled siRNA. Finding in the Western blot of the mice lung tumor homogenate was also consistent with inhibition of Cdc20 protein expression under systemic settings.

Discussion

RNA interference (RNAi) has advanced from its basic discovery to become a powerful genetic tool and arguably one of the most promising therapeutic modalities (Shankar, P. et al. 2005. JAMA 293: 1367-1373; Xie, F Y et al. 2006. Drug Discov Today 11: 67-73). In a therapeutic setting, siRNAs can be introduced either directly or as precursor molecules into a target cell through different strategies. The later includes either direct introduction of long, double-stranded RNA molecules or viral/nonviral delivery of DNAs, which are transcribed into long, double-stranded RNA molecules. This have been investigated by providing DNA vector constructs coding for short hairpin RNAs (shRNAs): The double-stranded region of the shRNA is formed through hairpin formation and intramolecular hybridization and is recognized by Dicer, leading to the formation of siRNAs/miRNA s homologous to the target gene of interest. Alternatively, shRNA molecules can be directly introduced into the cell. However, one major disadvantage of long double-stranded RNA molecules, either directly introduced or intracellularly transcribed, is the induction of a cellular immune response through activation of the interferon system. The direct delivery of siRNA/miRNA molecules into the target cell strategy largely avoids this problem, although some interferon-stimulating sequences are known as well. Furthermore, it does not require the action of Dicer (S. M. Elbashir, J. Harborth, W. Lendeckel, A. Yalcin, K. Weber, T. Tuschl. Nature 411 (2001) 494-498; Bridge A J, Pebernard S, Ducraux A, et al. Nat Genet 2003, 34, 263-264). Again, synthetic siRNA delivery to the cytosol of a cell should be easier to achieve, in principle, compared to plasmid based shRNA which must enter the nucleus and undergo transcription. However, the plasmid-born shRNA molecule has been established as a better substrate for Dicer and displays improved RISC loading (30. Kim, D. H. et al. 2005 (see comment). Nat Biotechnol 23: 222-226).

Cdc20 is an important cell cycle regulator required for the completion of mitosis in organisms from yeast to human. In the cell cycle, activation of the anaphase-promoting complex (APC) is a pre-requisite for anaphase initiation and for exit from mitosis. Cdc20 is one of the key regulators for APC; it binds and activates APC and the activated APC targets several mitotic regulators for degradation by ubiquitin-proteasome pathway. One of the major substrates of APC is the anaphase inhibitor securin. Before the onset of anaphase, securing binds to and inhibits separase, a ubiquitous protease. At the onset of anaphase, securin is degraded through ubiquitination by APC-Cdc20 complex and separase becomes free to cleave the components of the cohesion complex that holds the sister chromatids together at the metaphase of cell cycle. The pole ward force exerted on kinetochores then pulls the sister chromatids towards the opposite spindle poles. Since Cdc20 is highly expressed in several carcinomas, knockdown of the expression of Cdc20 through RNA interference holds therapeutic promise in combating cancer. These prior findings plus the high lung selective gene transfer efficiencies of guanidinylated cationic amphiphile 3 prompted us to explore therapeutic potential of Cdc20 siRNA entrapped in liposomes of lipid 3 toward inhibiting growth of secondary melanoma lung metastasis.

Guanidinylated cationic amphiphiles are, in general, efficient in delivering genetic materials into cells. Many distinguishing factors contribute to the high gene transfer efficiencies of guanidinylated cationic amphiphiles. The guanidinium head-groups remain protonated over a much wider range than other basic groups due to its remarkably high pka values (13.5) and therefore they strongly bind with polyanionic macromolecular DNA molecules under the physiological pH; in addition to forming electrostatic complexes with genetic materials, they form characteristic parallel zwitterionic N—H$^+$ . . . O$^-$ hydrogen bonds with the phosphate ions of the nucleotides and they are capable of forming hydrogen bonds with nucleic acid bases. Previously we have demonstrated that the guanidinylated cationic amphiphile with myristyl (n-C$_{14}$H$_{29}$) tail (lipid 1) is most efficient in delivering reporter gene into cultured animal cells at lipid:DNA charge ratio of 3:1 and 1:1. The findings in the model study using liposomally bound luciferase GL2 siRNA convincingly demonstrated the gene silencing efficiencies of lipid 1 in both A549 and B16F10 cells. Consistent with these in vitro findings using model luciferase GL2 siRNA, Cdc20 siRNA bound with the liposomes of lipid 1 was able to significantly inhibit the expression of Cdc20 both at protein and mRNA levels in B16F10 and A549 cells.

Cdc20 gene silencing efficiency of lipid 1 in B16F10 and A549 cells finally prompted us to evaluate the systemic potential of liposomally bound Cdc20 siRNA toward inhibiting growth of secondary lung metastasis. Interestingly, although lipid 1 with two myristyl chains was found to be most efficient in delivering siRNA under in vitro conditions, lipid 3 with two stearyl chains turned out to be the most active in delivering genes to mouse lung under systemic settings. Such contrasting hydrophobic chain length influence under in vitro and in vivo conditions is consistent with previously reported enhanced systemic efficacies of cationic amphiphiles with cyclic 3,4-dihydroxypyrrolidinium headgroup and two stearyl tails in delivering gene to mouse lung compared to its myristryl counterpart. Presumably, the longer stearyl chains make the liposomal systems more rigid and therefore more circulation stable under systemic settings. Thus, Cdc20 shRNA was complexed with a liposome of Lipid 3, DOPC, Cholesterol and DSPE-PEG-NH$_2$ in 1:1:1:0.05 molar ratios for evaluating its systemic potential in inhibiting growth of solid B16F10 tumors in C57BL/6J mice. Concordantly, a remarkable tumor regression was achieved for the mice treated with previously described liposomal Cdc20 shRNAs compared to the liposomal pCMV-β-gal treated and untreated mice. Likewise, Cdc20 siRNA was entrapped within the cationic liposomes of lung selective guanidinylated transfection lipid 3 with two stearyl chain for evaluating its systemic potential in inhibiting growth of secondary lung metastases. Toward evaluating whether such liposomally entrapped Cdc20 siRNA can be targeted to secondary lung metastatic tumor, we used an established lung metastasis model by intravenously injecting murine melanoma cells stably transduced with luciferase gene into C57BL/6J mice. Importantly, while intravenous administration of three consecutive doses of liposomally encapsulated Cdc20 siRNA reduced the number of lung metastatic nodules dramatically, the number of lung metastatic nodules remained high for untreated mice or for mice treated with control universal scrambled siRNA. Findings in the Western blot of the mice lung tumor homogenate, in the immunohistochemical and Hematoxylin & Eosin (H & E) staining of the lung tissue sections were also consistent with inhibition of Cdc20 protein expression under systemic settings. Toward gaining mechanistic insights into the arrest of any specific cell cycle step contributing to the inhibition of metastatic cell growth, finally we performed a flow cytometric experiments in B16F10 and A549 cells. Relative FACS profiles for the Cyclin B1 (a marker for the G2/M phase of cell cycle) in B16F10 and A549 cells treated with liposomally encapsulated Cdc20 siRNA with those for B16F10 and A549 cells treated with control universally scrambled siRNA and untreated B16F10 and A549 cells revealed significantly enhanced populations of G2/M phase for cells treated with liposomally bound Cdc20 siRNA. Thus, the observed inhibition of metastatic lung tumor growth by liposomally bound Cdc20 siRNA may originate from arrest of cell cycle in the G2/M phase. It is worth mentioning here that our present findings do not rule out possible off-target effects of Cdc20 siRNA contributing to the observed inhibition of lung metastases. Non-specific gene silencing resulting from binding of siRNA to sequences other than the specific target sequences have been reported. Remarkable inhibition of tumor growth was achieved only when the Cdc20 shRNA was administered in complexation with the above mentioned liposome. Similarly, no significant inhibition of tumor growth was observed when 5% aqueous glucose was administered alone. Mice intravenously administered with vehicle alone (5% aqueous glucose solution) developed large tumor on day 22 (FIG. 4A) and were sacrificed at that point.

In addition, off-target effects due to initiation or enhancement of the innate immune response by some motifs or patterns in the siRNA has been reported. Clearly, such possible off-target effects contribute to the observed inhibition of lung metastases to what growth will require further studies in future.

To conclude regarding the present invention, using an established experimental syngeneic model and lung metastasis model in C57BL/6J mice, we have demonstrated that intraperitoneal and intravenous administration of shRNA plasmids and 19 bp synthetic siRNA against Cdc20 (a key cell cycle regulator) encapsulated within the liposomes of a guanidinylated cationic amphiphile with stearyl tails inhibits B16F10 solid tumor growth and melanoma growth on lung. At the cellular level, we have shown that liposomally bound Cdc20 siRNA silences the expression of Cdc20 in B16F10 and A549 cells at both protein and mRNA levels. Flow cytometric analysis for the Cyclin B1 content (marker for G2/M phase of cell cycle) confirmed the presence of significantly enhanced populations of G2/M phase for cells treated with liposomally bound Cdc20 siRNA. To the best of our knowledge, this is the first demonstration for use of Cdc20 siRNA and shRNA for inhibiting growth of solid tumors and secondary lung metastasis in a mice model.

Synthesis of Lipid 2

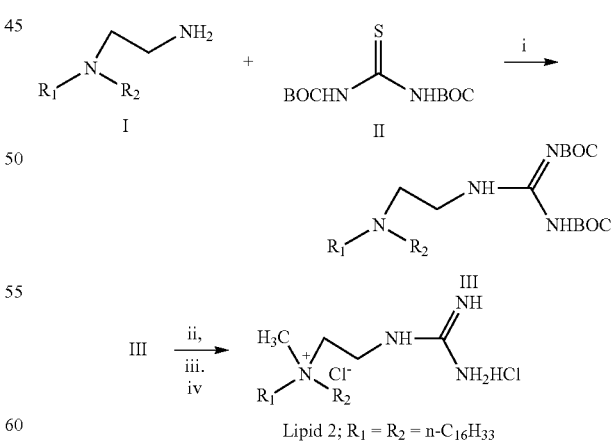

Lipid 2; R$_1$ = R$_2$ = n-C$_{16}$H$_{33}$

REAGENTS:
(i) HgCl$_2$ (1 eqv), TEA (1 eqv), DMF, N$_2$ atmp, 0° C.
(ii) MeI
(iii) TFA/DCM (1:1)
(iv) Cl ion exchange resin Advantage:

The present invention is the first report to show In vivo gene transfer efficiencies of lipids 1-3. It is well known to any practising scientist in the field that too many efficient liposomal formulations for delivering genes/siRNAs into cultured mammalian cells under in vitro conditions fail to transfer genes/siRNAs to specific body tissues under in vivo settings. The gene delivery efficiencies of our previously published liposomal formulations of lipids 1-3 containing equimolar cholesterol were tested only in vitro cultured cells (Sen, J and Chaudhuri, A. J. Med. Chem. 2005, 48, 812-820).

Figure 10:
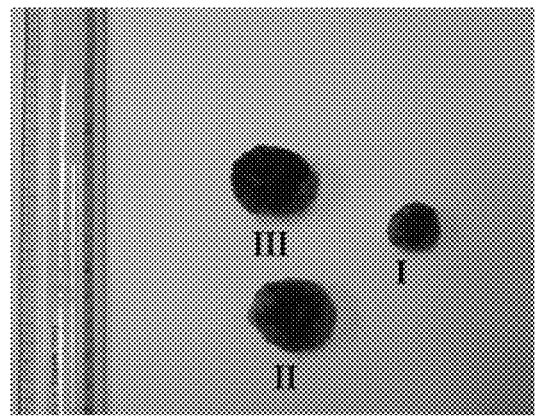
FIG. 10 shows solid tumor growth inhibition study liposomally associated Cdc20 shRNA in C57BL/6J mice. a. Representative samples of B16F10 tumors excised on day 23: I. Tumors treated with liposomes/Cdc20 shRNA complexes. II. Tumors treated with liposomes/-gal complexes. III. Tumor treated with vehicle only. b. Tumor growth inhibition study. 6-8 weeks old female C57BL/6 mice with aggressive B16F10 tumors (produced by subcutaneous injections of $1\times10^5$ B16F10 cells in 100 μL HBSS into the left flanks on day 0) were randomly sorted into two groups and each group (n=5) was administered intraperitonially with Lipid 3:DOPC:Chol:DSPE-PEG-NH$_2$ (1:1:1:0.05): Cdc20 shRNAs (50 µg) complex in 5% aqueous glucose, Lipid 3:DOPC:Chol:DSPE-PEG-NH$_2$ (1:1:1:0.05): -gal (50 µg) complex in 5% aqueous glucose and 5% aqueous glucose alone on day 15, 17, 19, 21 and 23. Each bar represents the mean of +/−SD for five mice (*p<0.005 compared to all controls). Tumor volumes (V=1/2.ab$^2$ where, a=maximum length of the tumor and b=minimum length of the tumor measured perpendicular to each other) were measured with a slide calipers.
Figure 10:
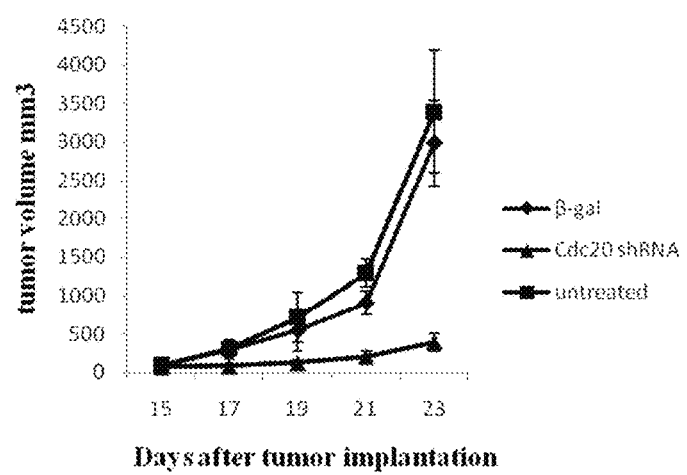

The presently disclosed formulations of 5 mM lipid 3 containing equimolar DOPC & Cholesterol and 5 mole % DSPE-PEG-$NH_2$ in complexation with CDC20shRNA is able to inhibit subcutaneously grown solid melanoma tumor in a syngeneic mouse model as shown in FIG. 10 of the present patent document.

The formulations disclosed in our prior patent (PCT/IN2010/000164) contained 1 mM lipid 1 with equimolar cholesterol and had no data which demonstrated in vivo efficiencies of inducing RNAi in specific body organs/tissues under in vivo settings.

The presently disclosed formulations of 5 mM lipid 3 with equimolar cholesterol in 5% aqueous glucose solution containing encapsulated CDC20siRNA is able to inhibit spontaneous growth of melanoma tumor on mouse lung in a secondary lung metastasis model as shown in FIG. 11a-b.

Importantly, the Western Blot (FIG. 11c) of the present patent document provides first evidence for in vivo RNAi using CDC20 siRNA in mouse model.

REFERENCES

U.S. Pat. Nos. 4,897,355 and 4,946,787 (1990) reported the synthesis and use of N-[.omega..(.omega.-1)-dialkyloxy]- and N-[..omega..(.omega.-1)-dialkenyloxy]-alk-1-yl-N, N,N-tetrasubstituted ammonium amphiphiles and their pharmaceutical formulations as efficient transfection vectors.

Leventis, R. and Silvius, J. R Biochim. Biophys. Acta. 1990; 1023: 124-132 reported the interactions of mammalian cells with lipid dispersions containing novel metabolizable cationic amphiphiles.

U.S. Pat. No. 5,264,618 (1993) reported the synthesis and use of additional series of highly efficient cationic lipids for intracellular delivery of biologically active molecules.

Felgner et al. J. Biol. Chem. 1994; 269: 2550-2561 reported enhanced gene delivery and mechanistic studies with a novel series of cationic lipid formulations.

U.S. Pat. No. 5,283,185 (1994) reported the synthesis and use of 3 [N—(N1,N1-dimethylaminoethane)carbamoyl] cholesterol, termed as "DC-Chol" for delivery of a plasmid carrying a gene for chloramphenicol acetyl transferase into cultured mammalian cells.

U.S. Pat. No. 5,283,185 (1994) reported the use of N-[2-[[2,5-bis[(3-aminopropyl)amino]-1-Oxopentyl]aminoethyl]-N,N-dimethyl-2,3-bis-(9-octadecenyloxy)-1-Propanaminium tetra(trifluoroacetate), one of the most widely used cationic lipids in gene delivery. The pharmaceutical formulation containing this cationic lipid is sold commercially under the trade name "Lipofectamine".

Solodin et al. Biochemistry 1995; 34: 13537-13544 reported a novel series of amphilic imidazolinium compounds for in vitro and in vivo gene delivery.

Wheeler et al. Proc. Natl. Acad. Sci. U.S.A. 1996; 93: 11454-11459 reported a novel cationic lipid that greatly enhances plasmid DNA delivery and expression in mouse lung.

U.S. Pat. No. 5,527,928 (1996) reported the synthesis and the use of N,N,N,N-tetramethyl-N,N-bis (hydroxy ethyl)-2,3-di(oleolyoxy)-1,4-butanediammonim iodide i.e pharmaceutical formulation as transfection vector.

U.S. Pat. No. 5,698,721 (1997) reported the synthesis and use of alkyl 0-phosphate esters of diacylphosphate compounds such as phosphatidylcholine or posphatidylethanolamine for intracellular delivery of macromolecules.

U.S. Pat. Nos. 5,661,018; 5,686,620 and 5,688,958 (1997) disclosed a novel class of cationic phospholipids containing phosphotriester derivatives of phosphoglycerides and sphingolipids efficient in the lipofection of nucleic acids.

U.S. Pat. No. 5,614,503 (1997) reported the synthesis and use of an amphiphatic transporter for delivery of nucleic acid into cells, comprising an essentially nontoxic, biodegradable cationic compound having a cationic polyamine head group capable of binding a nucleic acid and a cholesterol lipid tail capable of associating with a cellular membrane.

U.S. Pat. No. 5,705,693 (1998) disclosed the method of preparation and use of new cationic lipids and intermediates in their synthesis that are useful for transfecting nucleic acids or peptides into prokaryotic or eukaryotic cells. These lipids comprise one or two substituted arginine, lysine or ornithine residues, or derivatives thereof, linked to a lipophilic moiety.

U.S. Pat. No. 5,719,131 (1998) has reported the synthesis of a series of novel cationic amphiphiles that facilitate transport of genes into cells. The amphiphiles contain lipophilic groups derived from steroids, from mono or dialkylamines, alkylamines or polyalkylamines U.S. Pat. No. 5,527,928, (1996) reported on the synthesis and transfection biology of a novel cationic lipid namely, N,N,N',N'-tetramethyl-N,N'-bis(2-hydroxyethyl)-2,3-di (oleoyloxy)-1,4-butaneammonium iodide.

U.S. Pat. No. 6,541,649 (2003) disclosed novel cationic amphiphiles containing N-hydroxyalkyl head-group and its formulation for intracellular delivery of genetic materials.

U.S. Pat. No. 6,503,945 (2003) disclosed novel cationic amphiphiles containing N-hydroxyalkyl head-group and its formulation for intracellular delivery of genetic materials.

U.S. Pat. No. 7,101,995 (2006) disclosed a composition with low toxicity comprising an amphipathic compound, a polycation and a siRNA. The composition can be used for delivering siRNA into the cytoplasm of cultured mammalian cells.

U.S. Pat. No. 7,157,439 (2007) disclosed methods and compositions for improving and/or controlling wound healing by applying a wound care device comprising HoxD3 and HoxA3 and/or HoxB3 novel cationic amphiphiles containing N-hydroxyalkyl head-group and its formulation for intracellular delivery of genetic materials.

OTHER PUBLICATIONS

Behr, J. P. et al. Proc. Natl. Acad. Sci. USA, 1989; 86: 124-132.

Leventis, R. et al. Biochim. Biophys. Res. Commun 1991; 179: 280-285.

Akao, T. et al. Biochem. Mol. Biol. Int. 1994; 34: 915-920.

Felgner, J. H. et al. Proc. Natl. Acad. Sci. USA. 1996; 93: 11454-11459.
Bennett, M. J. et al. J. Med. Chem. 1997; 40: 4069-4078.
Blessing, T. et al. J. Am. Chem. Soc. 1998; 120: 8519-8520.
Wang, J. et al. J. Med. Chem. 1998; 41: 2207-2215.
Lim, Y. et al. J. Am. Chem. Soc. 1999; 121: 5633-5639.
Lim, Y. et al. J. J. Am. Chem. Soc. 2000; 122: 6524-6525.
Zhu, J. et al. J. Am. Chem. Soc. 2000; 122: 3252-3253.
Lynn, D. M.; Langer, R. J. Am. Chem. Soc. 2000; 122: 10761-10768.
Ferrari, M. E.; Rusalov, D.; Enas, J.; Wheeler, C. J.; Nuc. Acid. Res. 2001, 29, 1539-1548.
Banerjee, R.; Das, P. K.; Srilakshmi, G. V.; Chaudhuri, A.; Rao, N. M. J. Med. Chem. 1999, 42, 4292-4299.
Banerjee, R.; Mahidhar, Y. V.; Chaudhuri, A.; Gopal, V.; Rao, N. M. J. Med. Chem. 2001, 44, 4176-4185.
Singh, S. R.; Mukherjee, K.; Banerjee, R.; Chaudhuri, A.; Hait, S. K.; Moulik, S. P.; Ramadas, Y.; Vijayalakshmi, A.; Rao, N. M. Chem. Eur. J. (in press).
Floch, V.; Bolc'h, G. Le.; Gable-Guillaume, C.; Bris, N. Le.; Yaouanc, J-J.; Abbayes, H. Des.; Fe'rec, C.; Cle'ment, J-C. Eur. J. Med. Chem., 1998, 33, 923-934.
Solodin, I.; Brown, C.; Bruno, M.; Chow, S.; Jang, E-H.; Debs, R.; Heath, T. Biochemistry, 1995, 34, 13537-13544.
Mukherjee, K.; Bhattacharyya, J.; Ramakrishna, S.; Chaudhuri, A. J. Med. Chem. 2008, 51, 1967-1971.
Rajesh, M.; Sen, J.; Srujan, M.; Mukherjee, K.; Bojja, S.; Chaudhuri, A. J. Am. Chem. Soc. 2007, 129, 11408-11420.
Karmali, P. P.; Majeti, B. K.; Bojja S.; and Chaudhuri, A. Bioconjugate Chemistry 2006, 17, 159-171.
Bharat M. K.; Karmali, P. P.; Reddy, B. S.; Chaudhuri, A. J. Med. Chem. 2005, 48, 3784-3795.
Sen, J. and Chaudhuri, A. J. Med. Chem. 2005, 48, 812-820.
Sen, J. and Chaudhuri, A. Bioconjugate Chemistry 2005, 16, 903-912.
Bharat M. K.; Karmali, P. P.; Chaudhuri, A. Bioconjugate Chemistry 2005, 16, 676-684.
Mukherjee, K. M., Sen, J. and Chaudhuri, A. FEBS Letters 2005, 579, 1291-1300.
Mahidhar, Y. V., Rajesh, M.; Madhavendra, S. S.; Chaudhuri, A. J. Med. Chem. 2004, 47, 5721-5728.
Mahidhar, Y. V., Rajesh, M.; Chaudhuri, A. J. Med. Chem. 2004, 47, 3938-3948.
Valluripalli, V. K. and Chaudhuri, A. FEBS Letters 2004, 571, 205-211.
Singh, R. S.; Gonçalves, C.; Sandrin, P.; Pichon, C.; Midoux, P.; Chaudhuri, A. Chemistry and Biology 2004, 11, 713-723.
Majeti, B. K.; Singh, R. S.; Yadav, S. K.; Reddy, S. B.; Ramkrishna, S.; Diwan, P. V.;
Madhavendra, S. S.; Chaudhuri, A. Chemistry and Biology 2004, 11, 427-437.
Karmali, P. P.; Valluripalli, V. K.; Chaudhuri, A. J. Med. Chem. 2004, 47, 2123-2132.
Singh, R. S. and Chaudhuri, A. FEBS Letters 2004, 556, 86-90.
Kumar, V. V.; Pichon, C.; Refregiers, M.; Guerin, B.; Midoux, P.; Chaudhuri, A. Gene Therapy 2003, 10, 1206-1215.
Valluripalli, V. K.; Singh, R. S; Chaudhuri, A. Curr. Med. Chem. 2003, 10, 1297-1306.

The invention claimed is:

1. An in-vivo method for treating cancer in a warm-blooded animal, comprising administering a therapeutically effective amount of cationic liposomal composition to an animal, the therapeutically effective amount of the liposomal composition comprising a cationic lipid, a neutral co-lipid and a small RNA molecule, wherein the small RNAs selected from the group comprising small interfering RNA (siRNAs), plasmid DNA encoded short hairpin ribonucleic acid (shRNA) against Cdc20 (a key cell cycle regulator), wherein the molar ratio of cationic lipid to neutral lipid is 1:1; the administration of the therapeutically effective amount of the cationic liposomal composition inhibits tumour growth, wherein the tumour comprises a solid tumor or a secondary lung tumour and wherein the cdc20si RNA comprises a sequence selected from the group comprising SEQ ID No. 1 and SEQ ID No. 2.

2. The method of claim 1, wherein the liposomes have an average diameter in the range of 150-400 nm.

3. The method of claim 1, wherein the siRNA against Cdc20 is encapsulated within the intravesicular space of the liposomes.

4. The method of claim 1, wherein the shRNA against Cdc20 is electrostatically bound to the liposome.

5. The method of claim 1, wherein the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, menangioma, neuroblastoma, and retinoblastoma colorectal adnoma, malignant melanoma, uveal melanoma, primitive neuroectodermal tumor, papillary carcinoma of the thyroid, alveolar rhabdomyosarcoma, plemorphic adenoma of salivary glands, sporadic typical lipomas, extraskeletal nyxoidchondrosarcoma, mucoepidemoid carcinoma, adenolymphoma of salivary gland, intraabdominal desmoplastic small round cell tumor, askins tumor, ethesioneuroblastoma, uterine leiomyomas, and myxoid liposarcoma.

6. A method for treating cancer in a warm-blooded animal, comprising administering to an animal, a therapeutically effective amount of a composition, wherein the composition comprises a cationic liposomal composition and wherein the cationic liposomal composition comprises small RNAs selected from the group comprising, small interfering RNA (siRNAs), plasmid DNA encoded short hairpin ribonucleic acid (shRNA) against Cdc20 (a key cell cycle regulator) and wherein said amount of a composition inhibits tumour growth, wherein the tumour comprises a solid tumor or a secondary lung tumour and wherein the cdc20si RNA comprises a sequence selected from the group comprising SEQ ID No. 1, SEQ ID No. 2, SEQ ID No. 5 and SEQ ID No. 6.

7. The method of claim 6, comprising administering a composition comprising a cationic liposomes selected from the group comprising of small interfering ribonucleic acid (siRNA) or a plasmid DNA encoded short hairpin ribonucleic acid (shRNA) against CDC20.

8. The method of claim 6, wherein the liposomes have an average diameter in the range of 200-400 nm.

9. The method of claim 6, wherein the siRNA against CDC20 is encapsulated within the intravesicular space of the liposomes.

10. The method of claim 6, wherein the shRNA against CDC20 is electrostatically bound to the liposome.

11. The method of claim 6, wherein the tumor is selected from the group consisting of fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular tumor, lung carcinoma, small cell lung carcinoma, bladder carcinoma, epithelial carcinoma, glioma, glioblastoma, astrocytoma, medulloblastoma, craniopharyngioma, ependymoma, pinealoma, hemangioblastoma, acoustic neuroma, oligodendroglioma, menangioma, neuroblastoma, and retinoblastoma colorectal adnoma, malignant melanoma, uveal melanoma, primitive neuroectodermal tumor, papillary carcinoma of the thyroid, alveolar rhabdomyosarcoma, plemorphic adenoma of salivary glands, sporadic typical lipomas, extraskeletal nyxoidchondrosarcoma, mucoepidemoid carcinoma, adenolymphoma of salivary gland, intraabdominal desmoplastic small round cell tumor, askins tumor, ethesioneuroblastoma, uterine leiomyomas, and myxoid liposarcoma.

12. An in-vivo method for treating cancer in a warm-blooded animal, comprising administering a therapeutically effective amount of cationic liposomal composition to an animal, the therapeutically effective amount of the liposomal composition consisting of a cationic lipid, a neutral co-lipid and a small RNA molecule, wherein the small RNAs selected from the group comprising small interfering RNA (siRNAs), plasmid DNA encoded short hairpin ribonucleic acid (shRNA) against Cdc20 (a key cell cycle regulator), wherein the molar ratio of cationic lipid to neutral lipid is 1:1; the administration of the therapeutically effective amount of the cationic liposomal composition inhibits tumour growth and wherein the cdc20si RNA comprises a sequence selected from the group comprising SEQ ID No. 1, SEQ ID No. 2, SEQ ID No. 5 and SEQ ID No. 6.

13. The method of claim 12, wherein the co-lipid is selected from the group consisting of chloresterol, 1,2-dioleoyl-sn-glycero-3-phosphocholine (DOPC), aminopropyl polyethyleneglycol carbamyl-di stearoylphosphatidylethanolamine (DSPE-peg-$NH_2$).

14. An in-vivo method for treating cancer in a warm-blooded animal, comprising administering a therapeutically effective amount of cationic liposomal composition to an animal, the therapeutically effective amount of the liposomal composition consisting of a cationic lipid, a neutral co-lipid and a small RNA molecule, wherein the small RNAs selected from the group comprising small interfering RNA (siRNAs), plasmid DNA encoded short hairpin ribonucleic acid (shRNA) against Cdc20 (a key cell cycle regulator), wherein the ratio of cationic lipid to neutral lipid is 1:1; the administration of the therapeutically effective amount of the cationic liposomal composition inhibits tumour growth, wherein the cdc20si RNA comprises a sequence selected from the group comprising SEQ ID No. 1 and SEQ ID No. 2.

* * * * *

```
                               SEQUENCE LISTING

<160> NUMBER OF SEQ ID NOS: 6

<210> SEQ ID NO 1
<211> LENGTH: 21
<212> TYPE: DNA
<213> ORGANISM: Artificial Sequence
<220> FEATURE:
<223> OTHER INFORMATION: Synthetic human Cdc20 siRNA- (Sense Strand)

<400> SEQUENCE: 1
aguucguauc aaccuuaaat t                                                   21

<210> SEQ ID NO 2
<211> LENGTH: 21
<212> TYPE: DNA
<213> ORGANISM: Artificial Sequence
<220> FEATURE:
<223> OTHER INFORMATION: Synthetic human Cdc20 siRNA- (Antisense Strand)

<400> SEQUENCE: 2
uuuaaggaag auacgaacut g                                                   21

<210> SEQ ID NO 3
<211> LENGTH: 21
<212> TYPE: DNA
<213> ORGANISM: Artificial Sequence
<220> FEATURE:
<223> OTHER INFORMATION: Synthetic mouse Cdc20 siRNA- (Sense Strand)

<400> SEQUENCE: 3
ccaccaugau guucggguat t                                                   21
```

```
<210> SEQ ID NO 4
<211> LENGTH: 21
<212> TYPE: DNA
<213> ORGANISM: Artificial Sequence
<220> FEATURE:
<223> OTHER INFORMATION: Synthetic mouse Cdc20 siRNA- (Antisense Strand)

<400> SEQUENCE: 4
uacccgaaca ucaugguggt g                                              21

<210> SEQ ID NO 5
<211> LENGTH: 20
<212> TYPE: DNA
<213> ORGANISM: Artificial Sequence
<220> FEATURE:
<223> OTHER INFORMATION: Forward Primer - Cdc20

<400> SEQUENCE: 5
tccaaggttc agaccactcc                                                20

<210> SEQ ID NO 6
<211> LENGTH: 20
<212> TYPE: DNA
<213> ORGANISM: Artificial Sequence
<220> FEATURE:
<223> OTHER INFORMATION: Reverse Primer - Cdc20

<400> SEQUENCE: 6
gatccaggcc acagaggata                                                20
```